United States Patent
Pierce et al.

(10) Patent No.: US 12,414,568 B2
(45) Date of Patent: Sep. 16, 2025

(54) MICROBES, COMPOSITIONS, AND USES FOR INCREASING PLANT YIELD AND/OR DROUGHT TOLERANCE

(71) Applicant: Pro Farm Group, Inc., Davis, CA (US)

(72) Inventors: Brittany Pierce, Davis, CA (US); Ana Lucia Cordova-Kreylos, Davis, CA (US); Pamela G. Marrone, Davis, CA (US); Debora Wilk, Davis, CA (US)

(73) Assignee: Pro Farm Group, Inc., Davis, CA (US)

( * ) Notice: Subject to any disclaimer, the term of this patent is extended or adjusted under 35 U.S.C. 154(b) by 957 days.

(21) Appl. No.: 17/603,099

(22) PCT Filed: Mar. 12, 2020

(86) PCT No.: PCT/US2020/022346
§ 371 (c)(1),
(2) Date: Oct. 12, 2021

(87) PCT Pub. No.: WO2020/214290
PCT Pub. Date: Oct. 22, 2020

(65) Prior Publication Data
US 2022/0248683 A1     Aug. 11, 2022

Related U.S. Application Data

(60) Provisional application No. 62/879,632, filed on Jul. 29, 2019, provisional application No. 62/834,199, filed on Apr. 15, 2019.

(51) Int. Cl.
| | |
|---|---|
| *A01N 63/20* | (2020.01) |
| *A01N 63/22* | (2020.01) |
| *A01N 63/27* | (2020.01) |
| *A01N 63/28* | (2020.01) |
| *C05F 11/08* | (2006.01) |

(52) U.S. Cl.
CPC ............ *A01N 63/20* (2020.01); *A01N 63/22* (2020.01); *A01N 63/27* (2020.01); *A01N 63/28* (2020.01); *C05F 11/08* (2013.01)

(58) Field of Classification Search
None
See application file for complete search history.

(56) References Cited

U.S. PATENT DOCUMENTS

| | | |
|---|---|---|
| 2013/0150240 A1 | 6/2013 | Newman et al. |
| 2016/0113288 A1* | 4/2016 | Cordova-Kreylos ..... C12P 7/40 504/117 |
| 2017/0086466 A1 | 3/2017 | Marrone et al. |

OTHER PUBLICATIONS

Berendsen et al., The rhizosphere microbiome and plant health, Trends in Plant Science Aug. 2012, vol. 17, No. 8 (Year: 2012).*
Prashar et al. (Rhizosphere: its structure, bacterial diversity and significance, Rev Environ Sci Biotechnol (2014) 13:63-77) (Year: 2014).*
Belhaj et al. "Arabidopsis late blight: infection of a nonhost plant by Albugo laibachii enables full colonization by Phytophthora infestans," Cellular Microbiology: Jun. 15, 2016. (Year: 2016).*
International Search Report and Written Opinion dated Jul. 8, 2020, pp. 1-16.
Janda, J.M. et al.; "16S rRNA Gene Sequencing for Bacterial Identification in the Diagnostic Laboratory: Pluses, Perils, and Pitfalls"; Journal of Clinical Microbiology, vol. 45, No. 9, Sep. 2007; pp. 2761-2764.
Kothari, V.V. et al., "Genome Sequence of Salt-Tolerant Bacillus safensis Strain VK, Isolated from Saline Desert Area of Gujarat, India", Genome Announcements, Sep./Oct. 2013, vol. 1, Issue 5, p. 1.
Kumari, S. et al., "Induced drought tolerance through wild and mutant bacterial strain Pseudomonas simiae in mung pean (Vigna radiata L.)"; World J. Microbiol. Biotechnol. (2016) 32:4, pp. 1-10.
Satomi, M. et al., "Bacillus safensis sp. nov., isolated from spacecraft and assembly-facility surfaces," International Journal of Systematic and Evolutionary Microbiology (2006), 56, 1735-1740.
Strahsburger, E et al., "Draft Genome Sequence of Bacillus safensis RP10, Isolated from Soil in the Atacama Desert, Chile", Microbiology Resource Announcements, Oct. 31, 2019, vol. 8, Issue 44, pp. 1-2.
Wu, T. et al., "Characterization and Initial Application of Endophytic Bacillus safensis Strain ZY16 for Improving Phytoremediation of Oil-Contaminated Saline Soils", Frontiers in Microbiology, May 2019, vol. 10, Article 991, pp. 1-9.
Xu, J. et al., "Isolation and characterization of Bacillus subtilis strain 1-L-29, an endophytic bacteria from Camellia pleifera with antimicrobial activity and efficient plant-root colonization", PLOS ONE, Apr. 27, 2020, pp. 1-18.

\* cited by examiner

*Primary Examiner* — Louise W Humphrey
*Assistant Examiner* — Alexander M Duryee
(74) *Attorney, Agent, or Firm* — Dentons Durham Jones Pinegar; Sarah W. Matthews

(57) ABSTRACT

The present invention includes modified and unmodified microbes, compositions comprising these microbes, and methods of using these microbes and/or compositions for enhancing plant health, plant growth plant yield and/or drought tolerance. This disclosure also provides non-naturally occurring plant varieties that are artificially infected with microbes descried herein, as well as seed, reproductive tissue, vegetative tissue, regenerative tissues, plant parts, or progeny thereof.

17 Claims, 8 Drawing Sheets
Specification includes a Sequence Listing.

Figure 1: Weight per plot (g) evaluation treatment p-value < 0.327 and Rsq = 0.0775. Error bars represent the standard error.

Figure 2: Weight per Ear(g) evaluation treatment p-value < 0.090 and Rsq = 0.2409. Error bars represent the standard error.

Figure 3: Number of marketable ears evaluation treatment p-=value < 0.011 and Rsq = 0.2899. Error bars represent the standard error.

SEQUENCE LISTING

```
<160> NUMBER OF SEQ ID NOS: 11

<210> SEQ ID NO 1
<211> LENGTH: 1416
<212> TYPE: DNA
<213> ORGANISM: Flavobacterium hawainensis nov. sp H492
<220> FEATURE:
<221> NAME/KEY: misc_feature
<223> OTHER INFORMATION: 16S rDNA

<400> SEQUENCE: 1
gcttaccatg cagtcgaggg gtagaattct tcggaatttg agaccggcgc acgggtgcgt      60
aacgcgtatg caatctgcct ttcacagagg gatagcccag agaaatttgg attaatacct    120
catagtatta tggagtggca tcactttata attaaagtca caacggtgaa agatgagcat    180
gcgtcccatt agctagttgg taaggtaacg gcttaccaag gcgacgatgg gtaggggtcc    240
```

```
tgagagggag atcccccaca ctggtactga gacacggacc agacttatac gggaggcagc    300
agtgaggaat attggtcaat ggacgcaagt ctgaaccagc catgccgcgt gcaggatgac    360
ggtcctatgg attgtaaact gcttttgtac gagaagaaac acctctacgt gtagagactt    420
gacggtatcg taagaataag gatcggctaa ctccgtgcca gcagccgcgg taatacggag    480
gatccaagcg ttatccggaa tcattgggtt taaagggtct gtaggcggtc tagtaagtca    540
gtggtgaaag cccatcgctc aacggtggaa cggccattga tactgctgga cttgaattat    600
taggaagtaa ctagaatatg tagtgtagcg gtgaaatgct tagagattac atggaatacc    660
aattgcgaag gcaggttact actaatggat tgacgctgat ggacgaaagc gtgggtagcg    720
aacaggatta gataccctgg tagtccacgc cgtaaacgat ggatactagc tgttgggcgc    780
aagttcagtg gctaagcgaa agtgataagt atcccacctg gggagtacgg gcgcaagcct    840
gaaactcaaa ggaattgacg ggggcccgca caagcggtgg agcatgtggt ttaattcgat    900
gatacgcgag gaaccttacc aaggcttaaa tgtagtttga ccgatttgga aacagatctt    960
tcgcaagaca aattacaagg tgctgcatgg ttgtcgtcag ctcgtgccgt gaggtgtcag   1020
gttaagtcct ataacgagcg caaccccgtg tgttagttgc cagcgattcg gtcgggaact   1080
ctaacaagac tgccagtgca aactgtgagg aaggtgggga tgacgtcaaa tcatcacggc   1140
ccttacgcct tgggctacac acgtgctaca atggccggta cagagagcag ccacctcgcg   1200 aggggagcg aatctataaa gccggtcaca gttcggatcg gagtctgcaa ctcgactccg   1260
tgaagctgga atcgctagta atcggatatc agccatgatc cggtgaatac gttcccgggc   1320
cttgtacaca ccgcccgtca agccatggaa gctggggtg cctgaagtcg gtgaccgcaa   1380
ggagctgcct agggtaaaac tggtaactag ggctaa                            1416
```

<210> SEQ ID NO 2
<211> LENGTH: 1160
<212> TYPE: DNA
<213> ORGANISM: Bacillus megaterium H491
<220> FEATURE:
<221> NAME/KEY: misc_feature
<223> OTHER INFORMATION: 16S sequence

<400> SEQUENCE: 2

```
gacggagcaa cgccgcgtga gtgatgaagg ctttcgggtc gtaaaactct gttgttaggg     60
aagaacaagt acaagagtaa ctgcttgtac cttgacggta cctaaccaga aagccacggc    120
taactacgtg ccagcagccg cggtaatacg taggtggcaa gcgttatccg gaattattgg    180
gcgtaaagcg cgcgcaggcg gtttcttaag tctgatgtga aagcccacgg ctcaaccgtg    240
gagggtcatt ggaaactggg gaacttgagt gcagaagaga aaagcggaat tccacgtgta    300
gcggtgaaat gcgtagagat gtggaggaac accagtggcg aaggcggctt tttggtctgt    360
aactgacgct gaggcgcgaa agcgtgggga gcaaacagga ttagataccc tggtagtcca    420
cgccgtaaac gatgagtgct aagtgttaga gggtttccgc cctttagtgc tgcagctaac    480
gcattaagca ctccgcctgg ggagtacggt cgcaagactg aaactcaaag gaattgacgg    540
gggcccgcac aagcggtgga gcatgtggtt taattcgaag caacgcgaag aaccttacca    600
ggtcttgaca tcctctgaca actctagaga tagagcgttc ccttcgggg acagagtga     660 caggtggtgc atggttgtcg tcagctcgtg tcgtgagatg ttgggttaag tcccgcaacg    720
agcgcaaccc ttgatcttag ttgccagcat tcagttgggc actctaaggt gactgccggt    780
gacaaaccgg aggaaggtgg ggatgacgtc aaatcatcat gccccttatg acctgggcta    840
```

```
cacacgtgct acaatggatg gtacaaaggg ctgcaagacc gcgaggtcaa gccaatccca        900
taaaaccatt ctcagttcgg attgtaggct gcaactcgcc tacatgaagc tggaatcgct        960
agtaatcgcg gatcagcatg ccgcggtgaa tacgttcccg ggccttgtac acaccgcccg       1020
tcacaccacg agagtttgta acacccgaag tcggtggagt aaccgtaagg agctagccgc       1080
ctaaggtggg acagatgatt ggggtgaagt cgtaacaagg tagccgtatc ggaaggtgcg       1140
gctggatcac ctcctttcta                                                   1160
```

<210> SEQ ID NO 3
<211> LENGTH: 1445
<212> TYPE: DNA
<213> ORGANISM: Pseudomonas protegens CL45A
<220> FEATURE:
<221> NAME/KEY: misc_feature
<223> OTHER INFORMATION: 16S

<400> SEQUENCE: 3

```
catgcaagtc gagcggcagc acgggtactt gtacctggtg gcgagcggcg gacgggtgag         60
taatgcctag gaatctgcct agtagtgggg gataacgtcc ggaaacgggc gctaataccg        120
catacgtcct acgggagaaa gtgggggatc ttcggacctc acgctattag atgagcctag        180
gtcggattag ctagttggtg aggtaatggc tcaccaaggc gacgatccgt aactggtctg        240
agaggatgat cagtcacact ggaactgaga cacggtccag amtcctacgg gaggcagcag        300
tggggaatat tggacaatgg gcgaaagcct gatccagcca tgccgcgtgt gtgaagaagg        360
tcttcggatt gtaaagcact ttaagttggg aggaagggca gttacctaat acgtgattgt        420
tttgacgtta ccgacagaaa taagcaccgg ctaactctgt gcccagcagc cgcggtaata       480
cagagggtgc aagcgttaat cggaattact gggcgtaaag cgcgcgtagg tggtttgtta        540
agttggatgt gaaagccccg ggctcaacct gggaactgca tccaaaactg gcaagctaga        600
gtatggtaga gggtggtgga atttcctgtg tagcggtgaa atgcgtagat ataggaagga        660
acaccagtgg cgaaggcgac cacctggact gatactgaca ctgaggtgcg aaagcgtggg        720
gagcaaacag gattagatac cctggtagtc cacgccgtaa acgatgtcaa ctagccgttg        780
ggagccttga gctcttagtg gcgcagctaa cgcattaagt tgaccgcctg gggagtacgg        840
ccgcaaggtt aaaactcaaa tgaattgacg ggggcccgca caagcggtgg agcatgtggt        900
ttaattcgaa gcaacgcgaa gaaccttacc aggccttgac atccaatgaa ctttctagag        960
atagattggt gccttcggga acattgagac aggtgctgca tggctgtcgt cagctcgtgt       1020
cgtgagatgt tgggttaagt cccgtaacga gcgcaaccct tgtccttagt taccagcacg       1080
ttatggtggg cactctaagg agactgccgg tgacaaaccg gaggaaggtg gggatgacgt       1140
caagtcatca tggcccttc ggcctgggct acacacgtgc tacaatggtc ggtacaaagg       1200
gttgccaagc cgcgaggtgg agctaatccc ataaaaccga tcgtagtccg gatcgcagtc       1260
tgcaactcga ctgcgtgaag tcggaatcgc tagtaatcgc gaatcagaat gtcgcggtga       1320
atacgttccc gggccttgta cacaccgccc gtcacaccat gggagtgggt tgcaccagaa       1380
gtagctagtc taaccttcgg gaggacggtt accacggtgt gattcatgac tggggaagt       1440 cgaac                                                                   1445
```

<210> SEQ ID NO 4
<211> LENGTH: 1451
<212> TYPE: DNA
<213> ORGANISM: Enterobacter sp. nov 638

<220> FEATURE:
<221> NAME/KEY: misc_feature
<223> OTHER INFORMATION: 16S
<220> FEATURE:
<221> NAME/KEY: misc_feature
<222> LOCATION: (852)..(852)
<223> OTHER INFORMATION: n is a, c, g, or t

<400> SEQUENCE: 4

| | | | | | |
|---|---|---|---|---|---|
| ataatgcaag | tcgagcgaac | tgattagaag | cttgcttcta | tgacgttagc | ggcggacggg | 60 |
| tgagtaacac | gtgggcaacc | tgcctgtaag | actgggataa | cttcgggaaa | ccgaagctaa | 120 |
| taccggatag | gatcttctcc | ttcatgggag | atgattgaaa | gatggtttcg | gctatcactt | 180 |
| acagatgggc | ccgcggtgca | ttagctagtt | ggtgaggtaa | cggctcacca | aggcaacgat | 240 |
| gcatagccga | cctgagaggg | tgatcggcca | cactgggact | gagacacggc | ccagactcct | 300 |
| acgggaggca | gcagtaggga | atcttccgca | atggacgaaa | gtctgacgga | gcaacgccgc | 360 |
| gtgagtgatg | aaggctttcg | ggtcgtaaaa | ctctgttgtt | agggaagaac | aagtacaaga | 420 |
| gtaactgctt | gtaccttgac | ggtacctaac | cagaaagcca | cggctaacta | cgtgccagca | 480 |
| gccgcggtaa | tacgtaggtg | gcaagcgtta | tccggaatta | ttgggcgtaa | agcgcgcgca | 540 |
| ggcggtttct | taagtctgat | gtgaaagccc | acggctcaac | cgtggagggt | cattggaaac | 600 |
| tggggaactt | gagtgcagaa | gagaaaagcg | gaattccacg | tgtagcggtg | aaatgcgtag | 660 |
| agatgtggag | gaacaccagt | ggcgaaggcg | gcttttggt  | ctgtaactga | cgctgaggcg | 720 |
| cgaaagcgtg | gggagcaaac | aggattagat | accctggtag | tccacgccgt | aaacgatgag | 780 |
| tgctaagtgt | tagagggttt | ccgcccttta | gtgctgcagc | taacgcatta | agcactccgc | 840 |
| ctggggagta | cnggtcgcaa | gactgaaact | caaaggaatt | gacggggggcc | cgcacaagcg | 900 |
| gtggagcatg | tggtttaatt | cgaagcaacg | cgaagaacct | taccaggtct | tgacatcctc | 960 |
| tgacaactct | agagatagag | cgttcccctt | cggggggacag | agtgacaggt | ggtgcatggt | 1020 |
| tgtcgtcagc | tcgtgtcgtg | agatgttggg | ttaagtcccg | caacgagcgc | aacccttgat | 1080 |
| cttagttgcc | agcattcagt | tgggcactct | aaggtgactg | ccggtgacaa | accggaggaa | 1140 |
| ggtggggatg | acgtcaaatc | atcatgcccc | ttatgacctg | ggctacacac | gtgctacaat | 1200 |
| ggatggtaca | aagggctgca | agaccgcgag | gtcaagccaa | tcccataaaa | ccattctcag | 1260 |
| ttcggattgt | aggctgcaac | tcgcctacat | gaagctggaa | tcgctagtaa | tcgcggatca | 1320 |
| gcatgccgcg | gtgaatacgt | tcccgggcct | tgtacacacc | gcccgtcaca | ccacgagagt | 1380 |
| ttgtaacacc | cgaagtcggt | ggagtaaccg | taaggagcta | gccgcctaag | gtgggacaga | 1440 |
| tgattggggt | g | | | | | 1451 |

<210> SEQ ID NO 5
<211> LENGTH: 1437
<212> TYPE: DNA
<213> ORGANISM: Burkholderia megapolitana 0437
<220> FEATURE:
<221> NAME/KEY: misc_feature
<223> OTHER INFORMATION: 16S

<400> SEQUENCE: 5

| | | | | | |
|---|---|---|---|---|---|
| cttcctgcag | tcgaacggca | gcgcgggagc | aatcctggcg | gcgagtggcg | aacgggtgag | 60 |
| taatacatcg | gaacgtgtcc | tgtagtgggg | gatagcccgg | cgaaagccgg | attaataccg | 120 |
| catacgctct | acgaggaaaa | gggggggatc | ttaggacctc | tcgctacagg | ggcggccgat | 180 |
| ggcggattag | ctagttggtg | gggtaaaggc | ctaccaaggc | gacgatccgt | agctggtctg | 240 |

```
agaggacgac cagccacact gggactgaga cacggcccag actcctacgg gaggcagcag    300
tggggaattt tggacaatgg gggcaaccct gatccagcaa tgccgcgtgt gtgaagaagg    360
ccttcgggtt gtaaagcact tttgtccgga agaaatcat cctggttaat acctggggtg    420
gatgacggta ccggaagaat aagcaccggc taactacgtg ccagcagccg cggtaatacg    480
tagggtgcaa gcgttaatcg gaattactgg gcgtaaagcg tgcgcaggcg gttcgctaag    540
acagatgtga atccccggg cttaacctgg gaactgcatt tgtgactggc gggctagagt     600
atggcagagg ggggtagaat tccacgtgta gcagtgaaat gcgtagagat gtggaggaat    660
accgatggcg aaggcagccc cctgggccaa tactgacgct catgcacgaa agcgtgggga    720
gcaaacagga ttagataccc tggtagtcca cgccctaaac gatgtcaact agttgtcggg    780
tcttcattga cttggtaacg tagctaacgc gtgaagttga ccgcctgggg agtacggtcg    840
caagattaaa actcaaagga attgacgggg acccgcacaa gcggtggatg atgtggatta    900
attcgatgca acgcgaaaaa ccttacctac ccttgacatg tacggaatcc tgctgagaag    960
gtgggagtgc ccgaaaggga gccgtaacac akgtgctgca tgggctgtcg tcagctcgtg   1020
tcgtgagatg ttgggttaag tcccgcaacg agcgcaaccc ttgtccctag ttgctacgca   1080
agagcactcc agggagactg ccggtgacaa accggaggaa ggtggggatg acgtcaagtc   1140
ctcatggccc ttatgggtag ggcttcacac gtcatacaat ggtcggaaca gagggtcgcc   1200
aacccgcaag gggagccaa tcccagaaaa ccgatcgtag tccggatcgc agtctgcaac   1260
tcgactgcgt gaagctggaa tcgctagtaa tcgcggatca gcatgccgcg gtgaatacgt   1320
tcccgggtct gtacacacc gcccgtcaca ccatgggagt gggttttacc agaagtggct    1380
agtctaaccg caaggaggac ggtcaccacg gtaggattca tgactggggg aagtcga     1437
```

<210> SEQ ID NO 6
<211> LENGTH: 1520
<212> TYPE: DNA
<213> ORGANISM: Flavobacterium sacchrophilum R129
<220> FEATURE:
<221> NAME/KEY: misc_feature
<223> OTHER INFORMATION: 16S

<400> SEQUENCE: 6

```
tatacgatga agagtttgat cctggctcag gatgaacgct agcggcaggc ttaacacatg     60
caagtcgagg ggtatagttc ttcggaacta gagaccggcg cacgggtgcg taacgcgtat    120
gcaatctacc ttttacagag ggatagccca gagaaatttg gattaatacc tcatagtatt    180
atgaaatggc atcattttat aattaaagtc acaacggtaa aagatgagca tgcgtcccat    240
tagctagttg gtaaggtaac ggcttaccaa ggctacgatg gtagggggtc ctgagaggga    300
gatcccccac actggtactg agacacggac cagactccta cgggaggcag cagtgaggaa    360
tattggacaa tgggcgcaag cctgatccag ccatgccgcg tgcaggatga cggtcctatg    420
gattgtaaac tgctttata cgagaagaaa cactccgacg tgtcgagct tgacggtatc     480 gtaagaataa ggatcggcta actccgtgcc agcagccgcg gtaatacgga ggatccaagc    540
gttatccgga atcattgggt ttaaggggtc cgtaggcggt ttaataagtc agtggtgaaa    600
gcccatcgct caacggtgga acggccattg atactgttaa acttgaatta ttaggaagta    660
actagaatat gtagtgtagc ggtgaaatgc ttagagatta catggaatac caattgcgaa    720
ggcaggttac tactaatgga ttgacgctga tggacgaaag cgtgggtagc gaacaggatt    780
agataccctg gtagtccacg ccgtaaacga tggatactag ctgttggaag caatttcagt    840
```

```
ggctaagcga aagtgataag tatcccacct ggggagtacg ttcgcaagaa tgaaactcaa      900
aggaattgac gggggcccgc acaagcggtg gagcatgtgg tttaattcga tgatacgcga      960
ggaaccttac caaggcttaa atgtagtttg accgatttgg aaacagatct ttcgcaagac     1020
aaattacaag gtgctgcatg gttgtcgtca gctcgtgccg tgaggtgtca ggttaagtcc     1080
tataacgagc gcaaccctg ttgttagttg ccagcgagtc atgtcgggaa ctctaacaag     1140
actgccagtg caaactgtga ggaaggtggg gatgacgtca atcatcacg gcccttacgc     1200 cttgggctac acacgtgcta caatggccgg tacagagagc agccactggg cgaccaggag     1260
cgaatctata aaaccggtca cagttcggat cggagtctgc aactcgactc cgtgaagctg     1320
gaatcgctag taatcggata tcagccatga tccggtgaat acgttcccgg gccttgtaca     1380
caccgcccgt caagccatgg aagctggggg tgcctgaagt cggtgaccgc aaggagctgc     1440
ctagggtaaa actggtaact agggctaagt cgtaacaagg tagccgtacc ggaaggtgcg     1500
gctggaacac ctcctttcta                                                 1520

<210> SEQ ID NO 7
<211> LENGTH: 500
<212> TYPE: DNA
<213> ORGANISM: Ramularia sp. R223
<220> FEATURE:
<221> NAME/KEY: misc_feature
<223> OTHER INFORMATION: ITS

<400> SEQUENCE: 7
cggagggatc attactgagt gagggagcag tcccgacctc caacccttg tgaacgcatc        60 atgttgcttt gggggcgacc ctgccgtccg cggcattccc cccgaaggtc atcaaaacac      120
tgcattctta cgtcggagta taagttaat ttaataaaac tttcaacaac ggatctcttg      180
gttctggcat cgatgaagaa cgcagcgaaa tgcgataagt aatgtgaatt gcagaattca      240
gtgaatcatc gaatctttga acgcacattg cgcccctgg tattccgggg gcatgcctg       300 ttcgagcgtc atttcaccac tcaagcctcg cttggtattg ggcgtcgcga gtctctcgcg      360
cgcctcaaag tctccggctg agcggttcgt ctcccagcgt tgtggcaact atttcgcagt      420
ggagttcgag tcgtcgcggc cgttaaatct ttcaaaggtt gaccctcggat caggtaggga     480 tacccgctga acttaagcat                                                  500

<210> SEQ ID NO 8
<211> LENGTH: 1355
<212> TYPE: DNA
<213> ORGANISM: Streptomyces sp. R518
<220> FEATURE:
<221> NAME/KEY: misc_feature
<223> OTHER INFORMATION: 16S

<400> SEQUENCE: 8
cgtgggcaat ctgcccttca ctctgggaca agccctggaa acgggtcta ataccggata        60 ccactaccgc aggcatctgt ggtggttgaa agctccggcg gtgaaggatg agcccgcggc      120
ctatcagctt gttggtgagg taatggctca ccaaggcgac gacgggtagc cggcctgaga      180
gggcgaccgg ccacactggg actgagacac ggcccagact cctacgggag gcagcagtgg      240
ggaatattgc acaatgggcg aaagcctgat gcagcgacgc cgcgtgaggg atgacggcct      300
tcgggttgta aacctctttc agcagggaag aagcgaaagt gacggtacct gcagaagaag      360
cgccggctaa ctacgtgcca gcagccgcgg taatacgtag ggcgcaagcg ttgtccggaa      420
ttattgggcg taaagagctc gtaggcggct tgtcacgtcg ggtgtgaaag cccggggctt      480
```

```
aaccccgggt ctgcattcga tacgggctag ctagagtgtg gtaggggaga tcggaattcc    540
tggtgtagcg gtgaaatgcg cagatatcag gaggaacacc ggtggcgaag gcggatctct    600
gggccattac tgacgctgag gagcgaaagc gtggggagcg aacaggatta gataccctgg    660
tagtccacgc cgtaaacggt gggaactagg tgttggcgac attccacgtc gtcggtgccg    720
cagctaacgc attaagttcc ccgcctgggg agtacggccg caaggctaaa actcaaagga    780
attgacgggg gcccgcacaa gcagcggagc atgtggctta attcgacgca acgcgaagaa    840
ccttaccaag gcttgacata cgccggaaag catcagagat ggtgccccc ttgtggtcgg    900 tgtacaggtg gtgcatggct gtcgtcagct cgtgtcgtga gatgttgggt taagtcccgc    960
aacgagcgca acccttgtcc tgtgttgcca gcatgccctt cggggtgatg ggactcaca    1020 ggagaccgcc ggggtcaact cggaggaagg tggggacgac gtcaagtcat catgcccctt    1080
atgtcttggg ctgcacacgt gctacaatgg caggtacaat gagctgcgat accgtgaggt    1140
ggagcgaatc tcaaaaagcc tgtctcagtt cggattgggg tctgcaactc gacccatga    1200 agtcggagtt gctagtaatc gcagatcagc attgctgcgg tgaatacgtt cccgggcctt    1260
gtacacaccg cccgtcacgt cacgaaagtc ggtaacaccc gaagccggtg gcccaacccc    1320
ttgtgggagg gagctgtcga aggtgggact ggcga                                1355

<210> SEQ ID NO 9
<211> LENGTH: 1412
<212> TYPE: DNA
<213> ORGANISM: Streptomyces laurentii R914
<220> FEATURE:
<221> NAME/KEY: misc_feature
<223> OTHER INFORMATION: 16S

<400> SEQUENCE: 9
tgcagtcgaa cgatgaagcc cttcggggtg gattagtggc gaacgggtga gtaacacgtg     60
ggcaatctgc ccttcactct gggacaagcc ctggaaacgg ggtctaatac cggatacgac    120
ctgggaaggc atcttctcgg gtggaaagct ccggcggtga aggatgagcc gcgggcctat    180
cagcttgttg gtgaggtaac ggctcaccaa ggcgacgacg ggtagccggc ctgagagggc    240
gaccggccac actgggactg agacacggcc cagactccta cgggaggcag cagtggggaa    300
tattgcacaa tgggcgaaag cctgatgcag cgacgccgcg tgagggatga cggccttcgg    360
gttgtaaacc tctttcagca gggaagaagc gaaagtgacg gtacctgcag aagaagcgcc    420
ggctaactac gtgccagcag ccgcggtaat acgtagggcg caagcgttgt ccggaattat    480
tgggcgtaaa gagctcgtag gcggcttgtc acgtcgggtg tgaaagcccg ggcttaacc    540 ccgggtctgc atccgatacg ggcaggctag agtgtggtag gggagatcgg aattcctggt    600
gtagcggtga aatgcgcaga tatcaggagg aacaccggtg gcgaaggcgg atctctgggc    660
cattactgac gctgaggagc gaaagcgtgg ggagcgaaca ggattagata ccctggtagt    720
ccacgccgta acgttggga actaggtgtt ggcgacattc cacgttgtcg gtgccgcagc    780
taacgcatta agttccccgc ctggggagta cggccgcaag gctaaaactc aaaggaattg    840
acggggcccg cacaagcag cggagcatgt ggcttaattc gacgcaacgc gaagaacctt    900
accaaggctt gacatatacc ggaaacatcc agagatgggt gccccttgt ggtcggtata    960 caggtggtgc atggctgtcg tcagctcgtg tcgtgagatg ttgggttaag tcccgcaacg    1020
agcgcaaccc ttgtcctgtg ttgccagcat gcccttcggg gtgatgggga ctcacaggag    1080
accgccgggg tcaactcgga ggaaggtggg gacgacgtca agtcatcatg ccccttatgt    1140
```

-continued

```
cttgggctgc acacgtgcta caatggccgg tacaaagagc tgcgatgccg tgaggcggag    1200
cgaatctcaa aaagccggtc tcagttcgga ttggggtctg caactcgacc ccatgaagtc    1260
ggagttgcta gtaatcgcag atcagcattg ctgcggtgaa tacgttcccg ggccttgtac    1320
acaccgcccg tcacgtcacg aaagtcggta cacccgaag ccggtggccc aaccccttgt    1380
gggagggagc tgtcgaaggt gggactggcg at                                  1412
```

<210> SEQ ID NO 10
<211> LENGTH: 1430
<212> TYPE: DNA
<213> ORGANISM: Bacillus safensis R950
<220> FEATURE:
<221> NAME/KEY: misc_feature
<223> OTHER INFORMATION: 16S

<400> SEQUENCE: 10

```
gtcgagcgga cagaagggag cttgctcccg gatgttagcg gcggacgggt gagtaacacg     60
tgggtaacct gcctgtaaga ctgggataac tccgggaaac cggagctaat accggatagt    120
tccttgaacc gcatggttca aggatgaaag acggtttcgg ctgtcactta cagatggacc    180
cgcggcgcat tagctagttg gtggggtaat ggctcaccaa ggcgacgatg cgtagccgac    240
ctgagagggt gatcggccac actgggactg agacacggcc cagactccta cgggaggcag    300
cagtagggaa tcttccgcaa tggacgaaag tctgacggag caacgccgcg tgagtgatga    360
aggttttcgg atcgtaaagc tctgttgtta gggaagaaca gtgcgagag taactgctcg    420 caccttgacg gtacctaacc agaaagccac ggctaactac gtgccagcag ccgcggtaat    480
acgtaggtgg caagcgttgt ccggaattat tgggcgtaaa gggctcgcag gcggtttctt    540
aagtctgatg tgaaagcccc cggctcaacc ggggagggtc attggaaact gggaacttg     600 agtgcagaag aggagagtgg aattccacgt gtagcggtga aatgcgtaga gatgtggagg    660
aacaccagtg gcgaaggcga ctctctggtc tgtaactgac gctgaggagc gaaagcgtgg    720
ggagcgaaca ggattagata ccctggtagt ccacgccgta aacgatgagt gctaagtgtt    780
agggggtttc cgcccttag tgctgcagct aacgcattaa gcactccgcc tggggagtac    840
ggtcgcaaga ctgaaactca aaggaattga cgggggcccg cacaagcggt ggagcatgtg    900
gtttaattcg aagcaacgcg aagaaccta ccaggtcttg acatcctctg acaaccctag    960
agatagggct ttcccttcgg ggacagagtg acaggtggtg catggttgtc gtcagctcgt   1020
gtcgtgagat gttgggttaa gtcccgcaac gagcgcaacc cttgatctta gttgccagca   1080
ttcagttggg cactctaagg tgactgccgg tgacaaaccg gaggaaggtg gggatgacgt   1140
caaatcatca tgccccttat gacctgggct acacacgtgc tacaatggac agaacaaagg   1200
gctgcaagac cgcaaggttt agccaatccc ataaatctgt tctcagttcg gatcgcagtc   1260
tgcaactcga ctgcgtgaag ctggaatcgc tagtaatcgc ggatcagcat gccgcggtga   1320
atacgttccc gggccttgta cacaccgccc gtcacaccac gagagtttgc aacacccgaa   1380
gtcggtgagg taacctttat ggagccagcc gccgaaggtg gggcagatga              1430
```

<210> SEQ ID NO 11
<211> LENGTH: 583
<212> TYPE: DNA
<213> ORGANISM: Trichoderma sp. S089
<220> FEATURE:
<221> NAME/KEY: misc_feature
<223> OTHER INFORMATION: ITS -continued

```
<400> SEQUENCE: 11
gagggatcat taccgagttt acaactccca aacccaatgt gaacgttacc aaactgttgc     60
ctcggcggga tctctgcccc gggtgcgtcg cagccccgga ccaaggcgcc cgccggagga    120
ccaaccaaaa ctctttttgt ataccccctc gcgggttttt tataatctga gccttctcgg    180
cgcctctcgt aggcgtttcg aaaatgaatc aaaactttca acaacggatc tcttggttct    240
ggcatcgatg aagaacgcag cgaaatgcga taagtaatgt gaattgcaga attcagtgaa    300
tcatcgaatc tttgaacgca cattgcgccc gccagtattc tggcgggcat gcctgtccga    360
gcgtcatttc aaccctcgaa cccctccggg ggtcggcgt tggggatcgg ccctgcctct     420
tggcggtggc cgtctccgaa atacagtggc ggtctcgccg cagcctctcc tgcgcagtag    480
tttgcacact cgcatcggga gcgcggcgcg tccacagccg ttaaacaccc aacttctgaa    540
atgttgacct cggatcaggt aggaataccc gctgaactta agc                     583
```

MICROBES, COMPOSITIONS, AND USES FOR INCREASING PLANT YIELD AND/OR DROUGHT TOLERANCE

CROSS-REFERENCE TO RELATED APPLICATIONS

This application is a National Stage of International Application No. PCT/US2020/022346 filed on Mar. 12, 2020 and claims the priority of U.S. Provisional Application No. 62/834,199 filed on Apr. 15, 2019, and claims the priority of U.S. Provisional Application No. 62/879,632 filed Jul. 29, 2019. The contents of the foregoing applications are hereby incorporated by reference in their entirety.

TECHNICAL FIELD OF THE INVENTION

The present disclosure relates to compositions comprising microorganisms (bacteria and/or fungi) for increasing plant yield and/or increasing drought tolerance as well as methods for treating plants, plant parts, or soils thereof.

INCORPORATION-BY-REFERENCE OF MATERIALS FILED ON COMPACT DISC

The sequence listing that is contained in the file named "999-0006-US-PR2_ST25.txt," which is 20,480 bytes as measured in Microsoft Windows operating system and was created on Jul. 26, 2019, is filed electronically herewith and incorporated herein by reference.

BACKGROUND ART

Without limiting the scope of the invention, its background is described in connection with modified/unmodified microorganisms that increase plant yield and/or increasing drought tolerance.

Some microorganisms, including but not limited to bacteria and/or fungi, can positively affect plant health and growth under certain circumstances and improve yield and/or increasing drought tolerance of crop plants. Beneficial microbes and its metabolites can improve fertilization, nutrient availability or uptake, improve soil characteristics, modulate plant growth, or provide biopesticide or biocontrol activity. However, microbes can also negatively impact plants in some cases, and existing microbial products have sometimes exhibited inconsistent performance or minimal crop benefits.

Thus, there is a need which exists in the art for the development of novel microbial compositions and methods that can be used to improve yield and/or increasing drought tolerance of crop plants in a variety of agricultural field environments and growth conditions.

DISCLOSURE OF THE INVENTION

The present disclosure relates to microbial (bacteria and/or fungi) strains that have plant yield and/or drought tolerance enhancement properties, which include, but not limited to: *Flavobacterium hawaineses* nov sp. H492; *Bacillus megaterium* H491; *Pseudomonas protegens* (previously fluorescens) CL45A; *Enterobacter* sp. nov 638; *Bacillus safensis* R950; *Streptomyces* sp. R518; *Trichoderma* sp. S089; *Burkholderia megapolitana* O437; *Flavobacterium sacchrophilum* R129; *Ramularia* sp. R223; *Streptomyces laurentii* R914, or any combinations thereof.

In one aspect, the present disclosure relates to a composition comprising a whole cell broth collected from fermentation of *Flavobacterium hawaineses* nov sp. H492, *Bacillus megaterium* H491, *Pseudomonas protegens* CL45A, *Enterobacter* sp. nov 638, *Bacillus safensis* R950, *Streptomyces* sp. R518, *Trichoderma* sp. S089, *Burkholderia megapolitana* O437, *Flavobacterium sacchrophilum* R129, *Ramularia* sp. R223, and/or *Streptomyces laurentii* R914; and a carrier, diluent, or adjuvant, wherein said whole cell broth improves yield and/or drought tolerance of a plant or seed thereof.

In another aspect, the microbial strains are in the form of a composition comprising a whole cell broth collected from such microbial fermentation from the following modified and/or unmodified microbes: *Flavobacterium hawaineses* nov sp. H492; *Bacillus megaterium* H491; *Pseudomonas protegens* (previously known as *Pseudomonas fluorescens*) CL45A; *Enterobacter* sp. nov 638; *Bacillus safensis* R950; *Streptomyces* sp. R518; *Trichoderma* sp. S089; *Burkholderia megapolitana* O437; *Flavobacterium sacchrophilum* R129; *Ramularia* sp. R223; and/or *Streptomyces laurentii* R914.

In another aspect, the microbial strains are modified by heat-killed, and the whole cell broth collected from such microbial fermentation are contemplated in this disclosure. In one embodiment, the heat killing procedure is carried out post-fermentation.

According to another aspect, a bag or container is provided comprising or containing plant seeds or plant parts treated or coated with a microbial composition disclosed herein.

In an aspect, the present disclosure relates to a method to improves yield and/or drought tolerance of a plant or seed thereof comprising the step of applying said plant or seed thereof an effective amount of a composition comprising a whole cell broth collected from fermentation of *Flavobacterium hawaineses* nov sp. H492, *Bacillus megaterium* H491, *Pseudomonas protegens* CL45A, *Enterobacter* sp. nov 638, *Bacillus safensis* R950, *Streptomyces* sp. R518, *Trichoderma* sp. S089, *Burkholderia megapolitana* O437, *Flavobacterium sacchrophilum* R129, *Ramularia* sp. R223, and/or *Streptomyces laurentii* R914, and a carrier, diluent, or adjuvant, to improves yield and/or drought tolerance as compare to a control plant and/or seed thereof.

In other aspects, plants are provided that are grown or developed from a plant seed or plant part coated, treated or associated with a whole cell broth collected from microbial strain fermentation and/or microorganism isolate. In some embodiments, plants can exhibit increased yield/and or drought tolerance relative to a control plant grown or developed from a plant seed or plant part that was not coated, treated or associated with the microbial strain or isolate.

In certain embodiments, methods contemplated in this disclosure can comprise applying a composition disclosure herein to a plant seed, such as a corn, wheat, rice, barley, oat, sorghum or other cereal plant seed. In further embodiments, the applying step can comprise solid matrix priming, imbibing, coating, spraying, tumbling, agitating, dripping, soaking, immersing, dusting, drenching or encapsulating with the composition. In some embodiments, a composition can be applied to a crop plant, wherein the composition comprises an effective amount of a who cell broth collected from microbial strain fermentation, and/or modified or unmodified microbial isolate to increase the yield and/or drought tolerance of the crop plant. Such compositions can be applied to a plant part or plant seed, and the compositions can comprise an effective amount of a microbial strain or isolate to increase the yield/and or drought tolerance of a crop plant grown, developed or regenerated from the plant part or plant seed after planting.

In yet another aspect, methods of increasing the yield and/or drought tolerance of a crop plant are provided comprising: (a) applying to the crop plant a composition comprising a whole cell broth collected from modified or unmodified microbial strain fermentation and/or modified or unmodified microbial isolate and an agriculturally acceptable carrier, wherein the microbial strain or isolate is heterologous with respect to the crop plant, and wherein the microbial strain or isolate has whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding whole genome sequence of the bacterial strain(s) or isolate(s) such as *Flavobacterium hawaineses* nov sp. H492, *Bacillus megaterium* H491, *Pseudomonas protegens* CL45A, *Enterobacter* sp. nov 638, *Bacillus safensis* R950, *Streptomyces* sp. R518, *Trichoderma* sp. S089, *Burkholderia megapolitana* O437, *Flavobacterium sacchrophilum* R129, *Ramularia* sp. R223, and/or *Streptomyces laurentii* R914.

In another aspect, the present disclosure relates to a 16S rDNA or ITS (intergenic spacer region) sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to the 16S rDNA or ITS sequence of *Flavobacterium hawaineses* nov sp. H492, *Bacillus megaterium* H491, *Pseudomonas protegens* CL45A, *Enterobacter* sp. nov 638, *Bacillus safensis* R950, *Streptomyces* sp. R518, *Trichoderma* sp. S089, *Burkholderia megapolitana* O437, *Flavobacterium sacchrophilum* R129, *Ramularia* sp. R223, and/or *Streptomyces laurentii* R914.

In certain aspects, methods can further comprise harvesting seed from the crop plant. In some embodiments, a composition can be applied as a foliar treatment. In some embodiments, crop plants produced by methods described herein can exhibit greater yield and/or drought tolerance. In specific embodiments, the increased yield can result from increased biomass, increased grain weight per plot or per plant, greater resistance to lodging, increased root length, improved plant growth and vigor, increased stress tolerance, increased harvest index, increased fresh ear weight, increased ear diameter, increased ear length, increased seed size, increased seed number, or increased seed weight.

In further aspects, a plant, plant part or plant seed is provided that is associated with a composition described herein, such as a plant, plant part or plant seed having applied or coated on at least a portion of its outer surface a composition comprising a microbial strain or isolate, wherein the microbial strain or isolate is heterologous with respect to the plant, plant part or plant seed and has a 16S rDNA or ITS sequence that is at least 99.5%, at least 99.55%, at least 99.6%, at least 99.65%, at least 99.7%, at least 99.75%, at least 99.8%, at least 99.85%, at least 99.9% identical to *Flavobacterium hawaineses* nov sp. H492, *Bacillus megaterium* H491, *Pseudomonas protegens* CL45A, *Enterobacter* sp. nov 638, *Bacillus safensis* R950, *Streptomyces* sp. R518, *Trichoderma* sp. S089, *Burkholderia megapolitana* O437, *Flavobacterium sacchrophilum* R129, *Ramularia* sp. R223, or *Streptomyces laurentii* R914.

In certain embodiments, the composition can be applied or coated on at least a portion of the outer surface of the plant, plant part or plant seed. In some embodiments, the plant, plant part or plant seed is transgenic. Also provided is a plant, plant part or plant seed having applied or coated on at least a portion of its outer surface a composition comprising a microbial strain or isolate, wherein the microbial strain or isolate is heterologous with respect to the plant, plant part or plant seed and has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding whole genome sequence of the bacterial strain(s) or isolate(s) *Flavobacterium hawaineses* nov sp. H492, *Bacillus megaterium* H491, *Pseudomonas protegens* CL45A, *Enterobacter* sp. nov 638, *Bacillus safensis* R950, *Streptomyces* sp. R518, *Trichoderma* sp. S089, *Burkholderia megapolitana* O437, *Flavobacterium sacchrophilum* R129, *Ramularia* sp. R223, or *Streptomyces laurentii* R914.

In other aspects, plants are provided that are grown or developed from a plant seed or plant part coated, treated or associated with a whole cell broth collected from modified or unmodified microbial strain fermentation, and/or microbial isolate. In some embodiments, plants can exhibit increased yield and/or drought tolerance relative to a control plant grown or developed from a plant seed or plant part that was not coated, treated or associated with the microbial strain or isolate.

In further aspect, compositions can comprise a wetting agent or dispersant, a binder or adherent, an aqueous solvent and a non-aqueous co-solvent. Compositions can further comprise a pesticidal agent; a fungicide, herbicide, insecticide, miticide, acaricide, nematicide, and/or a plant nutrient or fertilizer. Compositions provided herein can be formulated as a solid; as a powder, lyophilisate, pellet or granules; as a liquid or gel; or as an emulsion, colloid, suspension or solution.

In some aspect, a method comprising one or more microbial strains are established as endophytes on the plant, after being applied to the plant, plant part or to the plant's surroundings. In some aspect, one or more microbial strains are established as endophytes on the plant in the reproductive tissue, vegetative tissue, regenerative tissues, plant parts, and/or progeny thereof. In some embodiments, one or more microbial strains are established as endophytes in the pollen of the plant. In some embodiments, one or more microbial strains are established as endophytes in the seed offspring of the plant that is exposed to or treated with a microbial strain, isolate, culture, or composition as described herein Yet in another aspect, the present disclosure provides a method of preparing a synthetic microbial consortium, comprising a) selecting a first set of microbes comprising one or more microbes that promote plant health, growth, yield, and/or drought tolerance; b) selecting a second set of microbes comprising one or more microbes that increase the competitive fitness of the first set of microbes in step a); and c) combining these microbes into a single mixture and designating the combination as a synthetic consortium. In some aspect, the method comprises a further step of applying the synthetic consortium as described herein to a plant (or a part thereof), a seed, or a seedling. The present embodiments also provide a synthetic microbial consortium prepared as described herein. The present embodiments further provide a method of promoting plant health, plant growth and/or plant yield, comprising applying a synthetic microbial consortium prepared as described herein to a plant, a plant part, or the plant's surroundings.

In one aspect, the microbial (bacteria or fungi) strains have the following NRRL numbers: *Trichoderma* sp. S089 (NRRL-67808), *Bacillus safensis* R950 (NRRL B-67775), *Streptomyces* sp. R518 (NRRL B-67773), *Burkholderia megapolitana* O437 (NRRL B-67776), *Flavobacterium sacchrophilum* R129 (NRRL B-67772), *Ramularia* sp. R223 (NRRL 67807), and/or *Streptomyces laurentii* R914 (NRRL B-67774), wherein all of the above were deposited on May 31, 2019.

DESCRIPTION OF THE DRAWINGS

For a more complete understanding of the features and advantages of the present invention, reference is now made to the detailed description of the invention along with the accompanying figures and in which.

DESCRIPTION OF THE INVENTION

Figure 1:
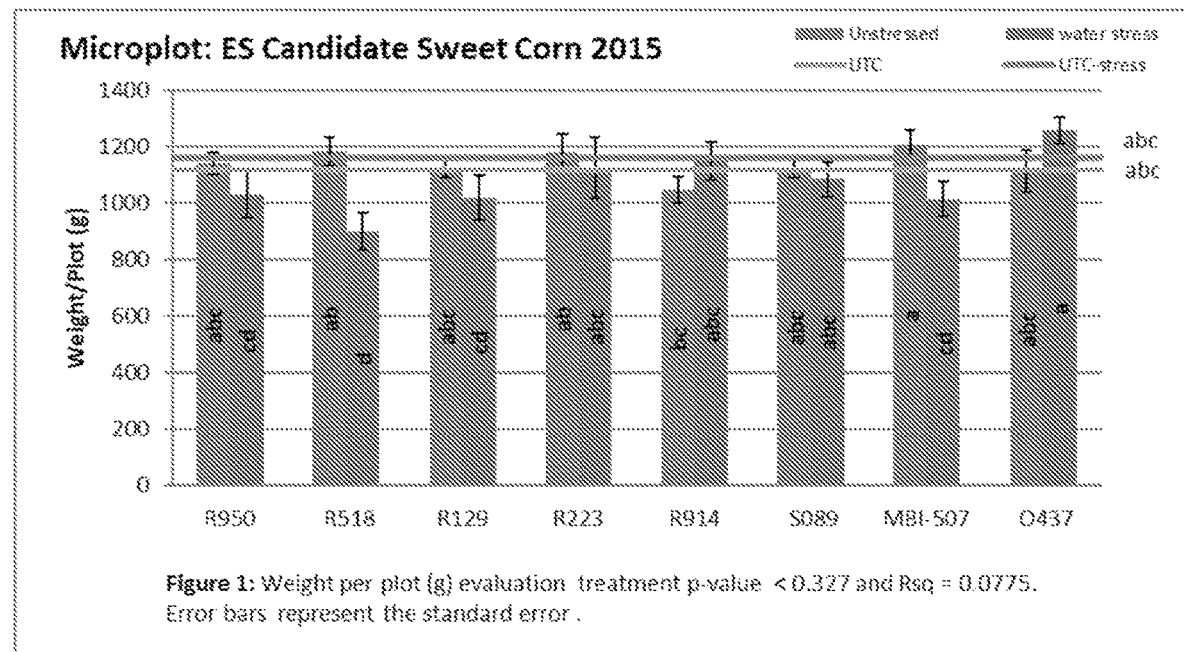
FIG. 1 denotes weight/plot (g) of various strains on corn. Weight per plot evaluation treatment p-value<0.327 and Rsq=0.0775. Error bars represent standard error. UTC stands for untreated control.
Figure 2:
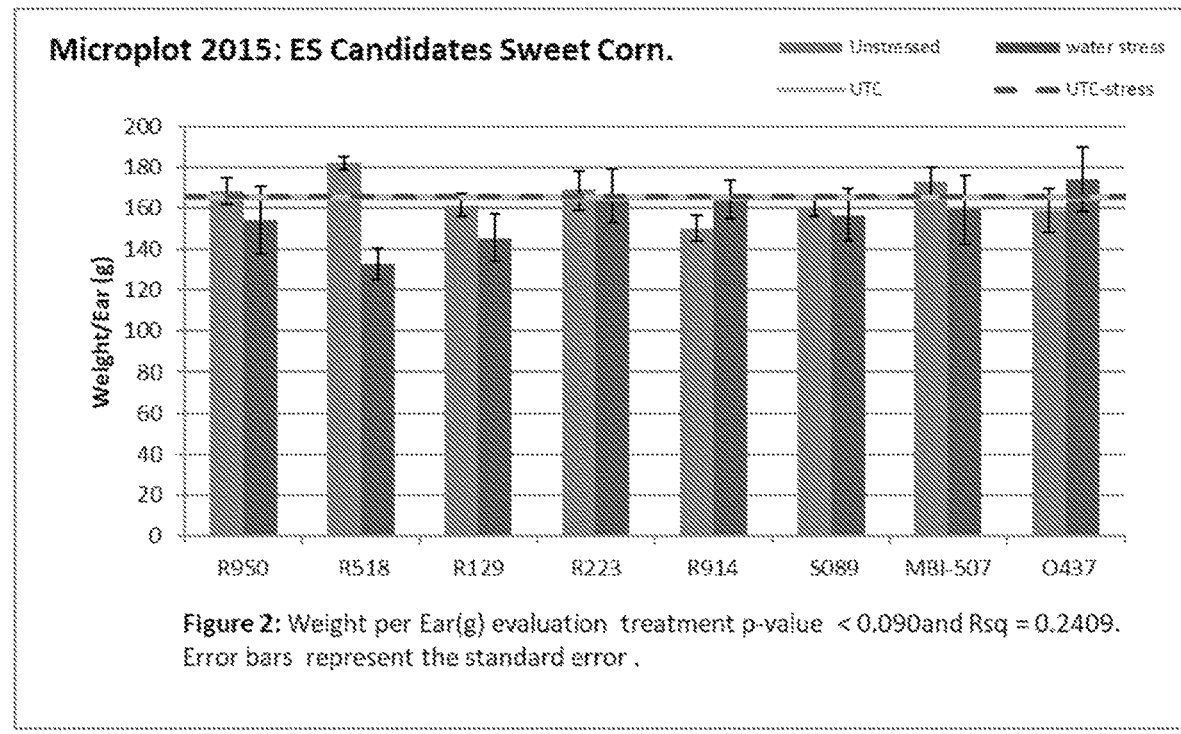
FIG. 2 denotes weight/ear (g) of various strains on corn. Weight per plot evaluation treatment p-value<0.090 and Rsq=0.2409. Error bars represent standard error. UTC stands for untreated control.
Figure 3:
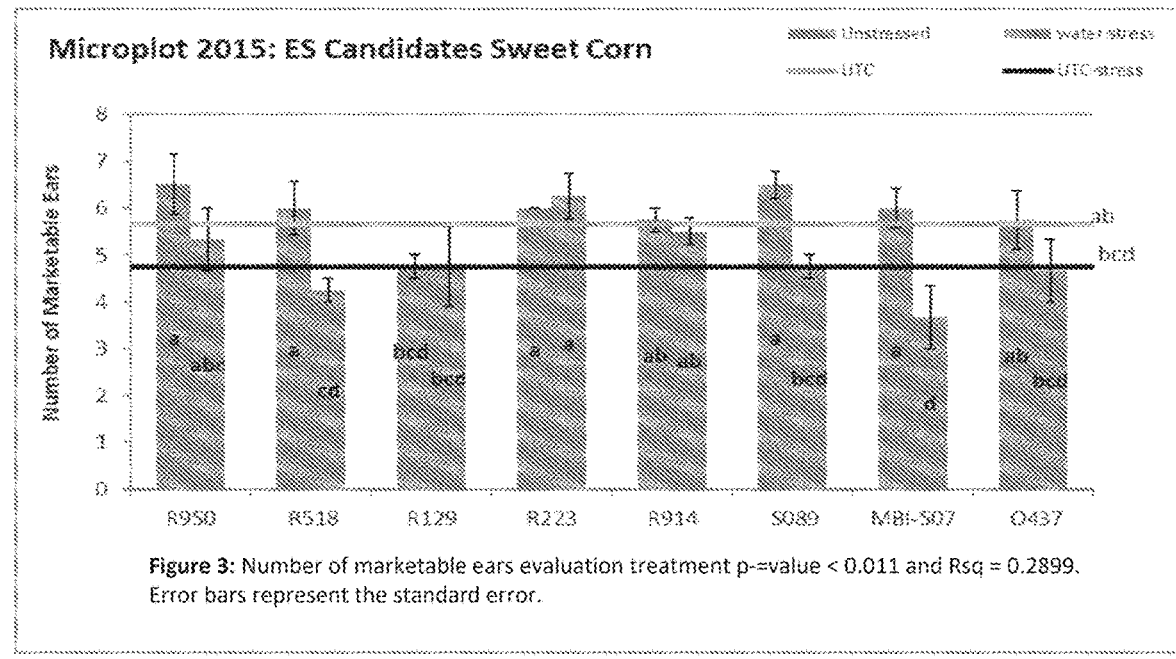
FIG. 3 denotes number of marketable ears of various strain son corn. Weight per plot evaluation treatment p-value<0.011 and Rsq=0.2899. Error bars represent standard error. UTC stands for untreated control.
Figure 4:
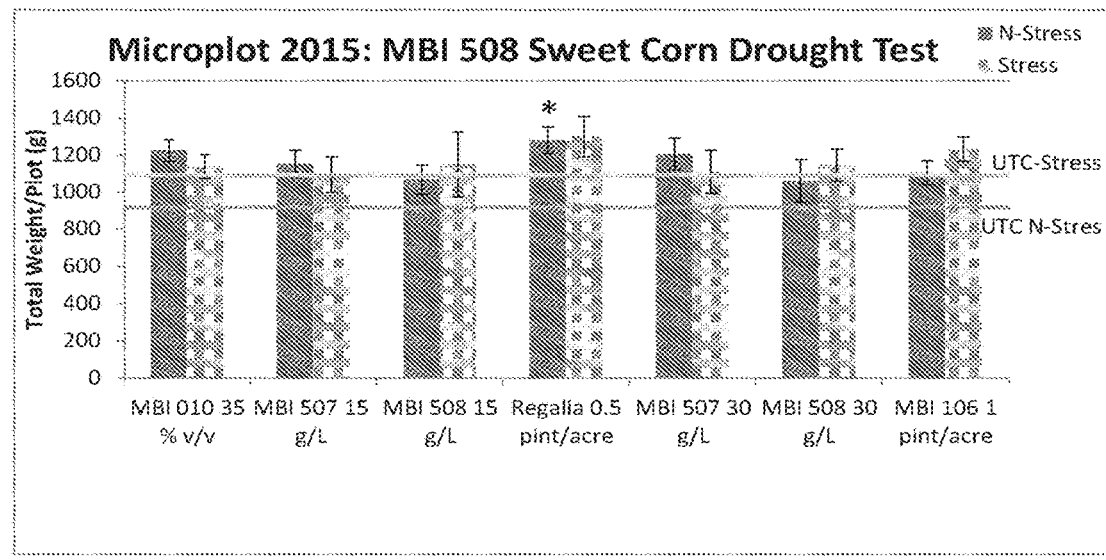
FIG. 4 denotes total weight per plot of various trains on corn in drought condition. Weight per plot evaluation treatment p-value<0.537 and Rsq=0.00. Error bars represent standard error. UTC stands for untreated control.
Figure 5:
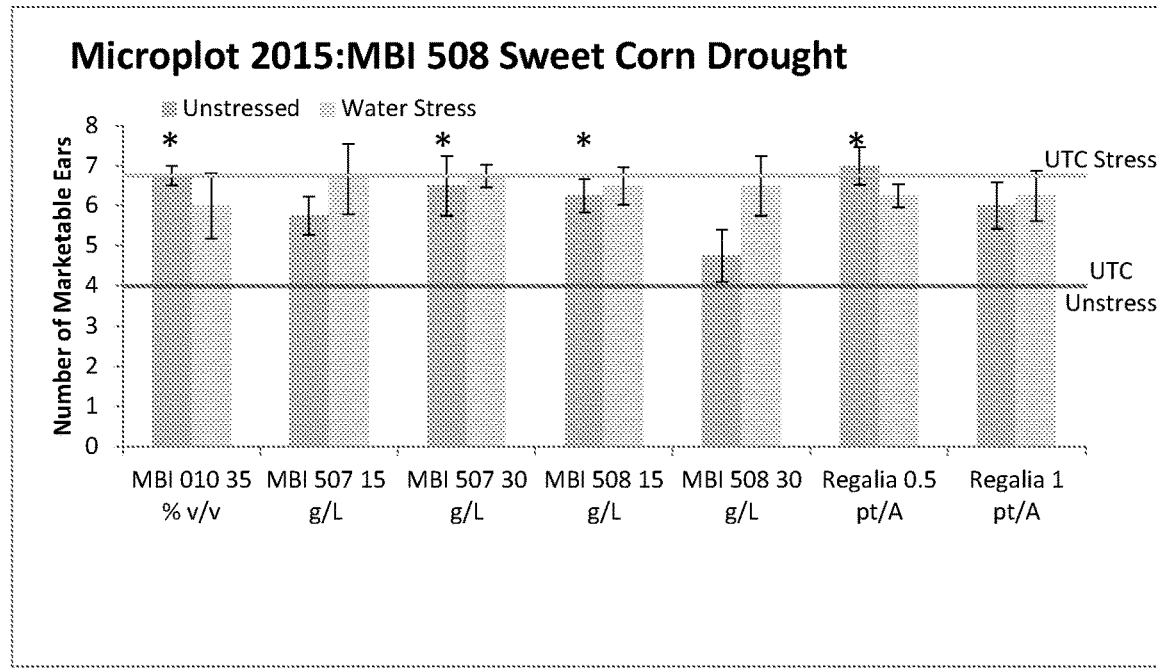
FIG. 5 denotes number of marketable ears per various strains under drought condition. Evaluation treatment p-value<0.167 and Rsq=0.066. Error bars represent standard error. UTC stands for untreated control.
Figure 6:
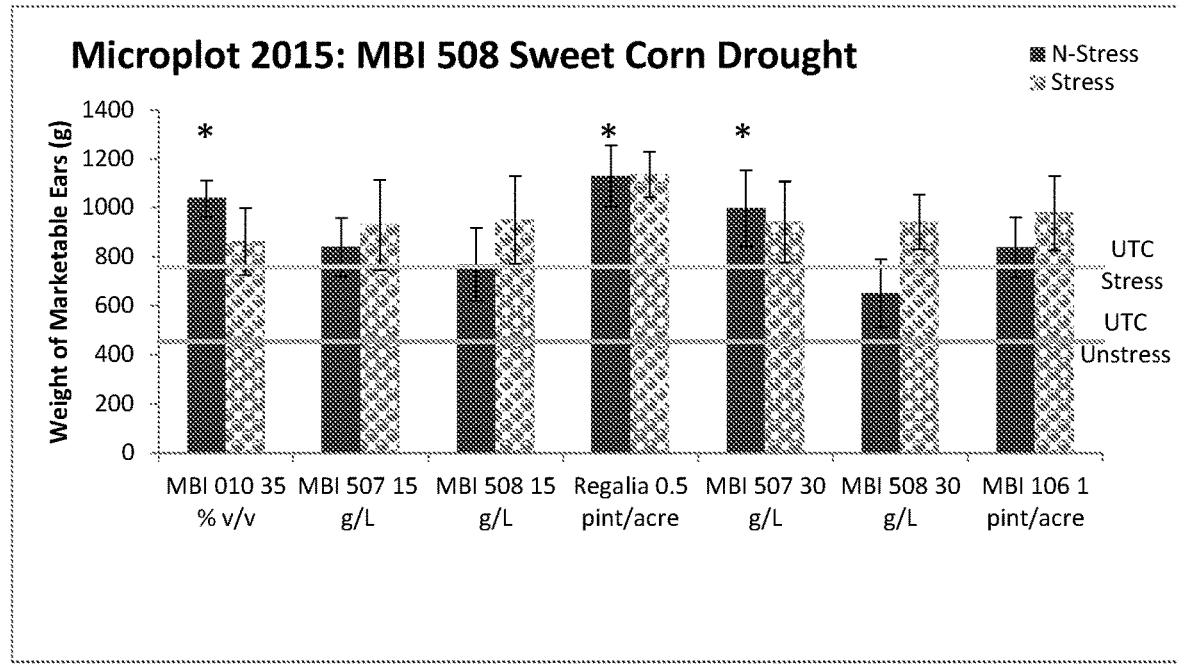
FIG. 6 denotes number of marketable ears per various strains under drought condition. Evaluation treatment p-value<0.220 and Rsq=0.5830. Error bars represent standard error. UTC stands for untreated control.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "whole cell broth" refers to a liquid culture containing both microbial cells and media. If bacteria are grown on a plate the cells can be harvested in water or other liquid, whole culture.

The term "supernatant" refers to the liquid remaining when cells that are grown in broth or harvested in another liquid from an agar plate are removed by centrifugation, filtration, sedimentation, or other means well known in the art.

As used herein, "filtrate" refers to liquid from a whole broth culture that has passed through a membrane.

As used herein, "extract" refers to liquid substance removed from cells by a solvent (water, detergent, buffer) and separated from the cells by centrifugation, filtration or other method.

As used herein, "metabolite" refers to a compound, substance or byproduct of a fermentation of a microorganism, or supernatant, filtrate, or extract obtained from a microorganism that has increase plant yield activity.

As used herein, an isolated strain of a microbe is a strain that has been removed from its natural milieu. As such, the term "isolated" does not necessarily reflect the extent to which the microbe has been purified. But, in different embodiments, an "isolated" culture has been purified at least 2× or 5× or 10× or 50× or 100× from the raw material from which it is isolated. As a non-limiting example, if a culture is isolated from soil as raw material, the organism can be isolated to an extent that its concentration in a given quantity of purified or partially purified material (e.g., soil) is at least 2× or 5× or 10× or 50× or 100× of that in the original raw material.

A "substantially pure culture" of the strain of microbe refers to a culture which contains substantially no other microbes than the desired strain or strains of microbe. In other words, a substantially pure culture of a strain of microbe is substantially free of other contaminants, which can include microbial contaminants as well as undesirable chemical contaminants.

As used herein, a "biologically pure" strain is intended to mean the strain separated from materials with which it is normally associated in nature. A strain associated with other strains, or with compounds or materials that it is not normally found with in nature, is still defined as "biologically pure." A monoculture of a particular strain is, of course, "biologically pure." In different embodiments, a "biologically pure" culture has been purified at least 2× or 5× or 10× or 50× or 100× or 1000× or higher (to the extent considered feasible by a skilled person in the art) from the material with which it is normally associated in nature. As a non-limiting example, if a culture is normally associated with soil, the organism can be biologically pure to an extent that its concentration in a given quantity of purified or partially purified material with which it is normally associated (e.g. soil) is at least 2× or 5× or 10× or 50× or 100×, or 1000× or higher (to the extent considered feasible by a skilled person in the art) that in the original unpurified material.

As used herein, the terms "percent identity", "% identity" or "percent identical" as used herein in reference to two or more nucleotide or protein sequences is calculated by (i) comparing two optimally aligned sequences over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, as used herein, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

An "effective amount", as used herein, is an amount sufficient to effect beneficial and/or desired results such as increasing yield and/or drought tolerance. An effective amount can be administered in one or more administrations. In terms of treatment, inhibition or protection, an effective amount is that amount sufficient to ameliorate, stabilize, reverse, slow or delay progression of the target infection, abiotic stress, or disease state. The expression "effective microorganism" used herein in reference to a microorganism is intended to mean that the subject strain exhibits a degree of promotion of plant health, growth and/or yield or a degree of inhibition of a pathogenic disease that exceeds, at a statistically significant level, that of an untreated control. In some instances, the expression "an effective amount" is used herein in reference to that quantity of microbial treatment which is necessary to obtain a beneficial or desired result relative to that occurring in an untreated control under suitable conditions of treatment as described herein. For example, the expression "an agriculturally effective amount" is used herein in reference to that quantity of microbial treatment which is necessary to obtain an agriculturally beneficial or desired result relative to that occurring in an untreated control under suitable conditions of treatment as described herein. The effective amount of an agricultural formulation or composition that should be applied for the improvement of plant health, growth, tolerance to drought, and/or yield, for the control of, e.g., insects, plant diseases, or weeds, can be readily determined via a combination of general knowledge of the applicable field.

A "nutrient" as used herein means a compound or composition that is able to provide one or more nutrient elements to plants. In some embodiments, a nutrient provides one or more nutrient elements selected from nitrogen (N), phosphorus (P), potassium (K), calcium (Ca), magnesium (Mg), sulfur (S), iron (Fe), manganese (Mn), zinc (Zn), copper (Cu), nickel (Ni), boron (B) and molybdenum (Mo) to the plants. In some embodiments, a nutrient as used herein provides at least one of nitrogen (N), phosphorus (P) and potassium (K) to the plants. In some embodiments, a nutrient provides at least one of calcium (Ca), magnesium (Mg) and sulfur (S) to the plants. In some embodiments, a nutrient of the embodiments of this application provides at least one of iron (Fe), manganese (Mn), zinc (Zn), copper (Cu), nickel (Ni), boron (B) and molybdenum (Mo) to the plants. In some embodiments, a nutrient is a compound or composition that promotes the plant uptake of one or more nutrient elements selected from nitrogen (N), phosphorus (P), potassium (K), calcium (Ca), magnesium (Mg), sulfur (S), iron (Fe), manganese (Mn), zinc (Zn), copper (Cu), nickel (Ni), boron (B) and molybdenum (Mo), from the soil.

A "fertilizer" as used herein means a compound or composition that is added to plants or soil to improve plant health, growth and/or yield. In some embodiments, a fertilizer improves plant health, growth and/or yield by providing a nutrient (such as the ones described herein) to the plant. Fertilizers include, but are not limited to, inorganic fertilizers, organic (or natural) fertilizers, granular fertilizers and liquid fertilizers. Granular fertilizers are solid granules, while liquid fertilizers are made from water soluble powders or liquid concentrates that mix with water to form a liquid fertilizer solution. In some embodiments, plants can quickly take up most water-soluble fertilizers, while granular fertilizers may need a while to dissolve or decompose before plants can access their nutrients. High-tech granular fertilizers have "slow-release," "timed-release," or "controlled-release" properties, synonymous terms meaning that they release their nutrients slowly over a period of time. Organic fertilizer comes from an organic source such as, but not limited to, compost, manure, blood meal, cottonseed meal, feather meal, crab meal, or others, as opposed to synthetic sources. There are also some natural fertilizers that are not organic, such as Greensand, which contain potassium, iron, calcium, and other nutrients. These are considered suitable for organic gardening because they are not synthesized, but come from natural mineral-rich deposits in the earth. Organic fertilizers depend on the microbes in the soil to break them down into digestible bits for plants. In some embodiments, organic fertilizers encourage soil microbes, earthworms, and other flora more than synthetic fertilizers do, because most organic fertilizers don't add excess salts and acid to the soil. Inorganic fertilizers are also known as synthetic or artificial fertilizers. Inorganic fertilizers are manufactured.

As used herein, an "endophyte" is an endosymbiont that lives within a plant for at least part of its life. Endophytes can be transmitted either vertically (directly from parent to offspring) or horizontally (from individual to unrelated individual). In some embodiments, vertically-transmitted fungal endophytes are asexual and transmit from the maternal plant to offspring via fungal hyphae penetrating the host's seeds. Bacterial endophytes can also be transferred vertically from seeds to seedlings (Ferreira et al., FEMS Microbiol. Lett. 287:8-14, 2008). In some embodiments, horizontally-transmitted endophytes are typically sexual, and transmit via spores that can be spread by wind and/or insect vectors. Microbial endophytes of crop plants have received considerable attention with respect to their ability to control disease and insect infestation, as well as their potential to promoting plant growth. For instance, some microbial strains described herein can be able to establish as endophytes in plants that come in contact with them. Such microbial strains are microbial endophytes.

As used herein, the term "yield" refers to the amount of harvestable plant material or plant-derived product, and is normally defined as the measurable produce of economic value of a crop. For crop plants, "yield" also means the amount of harvested material per acre or unit of production. Yield can be defined in terms of quantity or quality. The harvested material can vary from crop to crop, for example, it can be seeds, above ground biomass, roots, fruits, cotton fibers, any other part of the plant, or any plant-derived product which is of economic value.

The term "yield" also encompasses yield potential, which is the maximum obtainable yield. Yield may be dependent on a number of yield components, which can be monitored by certain parameters. These parameters are well known to persons skilled in the art and vary from crop to crop. The term "yield" also encompasses harvest index, which is the ratio between the harvested biomass over the total amount of biomass.

As used herein, "drought," "drought conditions," "water-limited conditions," or "water-deficit conditions" refer to a stress condition having a moisture deficit in the soil.

In one embodiment, a way to characterize drought conditions is using Palmer Drought Severity Index (PDSI), which is a drought indicator to assess moisture status. PDSI uses temperature and precipitation data to calculate water supply and demand, and also incorporates soil moisture. Drought conditions, according to their different severity can has a PDSI of −1.0 to −1.9 (abnormally dry), a PDSI of −2.0 to −2.9 (moderate drought), a PDSI of −3.0 to −3.9 (severe drought), a PDSI of −4.0 to −4.9 (extreme drought), or a PDSI of −5.0 or less (exceptional drought). Alternatively, drought tolerance can be expressed by percentage of plany yield increase vs. a control plant.

A "control plant", as used herein, provides a reference point for measuring changes in phenotype of the subject plant, and can be any suitable plant cell, seed, plant component, plant tissue, plant organ or whole plant. A control plant can comprise, for example (but not limited to), (a) a wild-type plant or cell, i.e., of the same genotype as the starting material for the genetic alteration which resulted in the subject plant or cell; (b) a plant or cell of the genotype as the starting material but which has been transformed with a null construct (i.e., a construct which has no known effect on the trait of interest, such as a construct comprising a reporter gene); (c) a plant or cell which is a non-transformed segregant among progeny of a subject plant or cell; (d) a plant or cell which is genetically identical to the subject plant or cell but which is not exposed to the same treatment (e.g., inoculant treatment) as the subject plant or cell; (e) the subject plant or cell itself, under conditions in which the gene of interest is not expressed; or (f) the subject plant or cell itself, under conditions in which it has not been exposed to a particular treatment such as, for example, an inoculant or combination of inoculants, microbial strains, and/or other chemicals. "Inoculant" as used herein refers to any culture or preparation that comprises at least one microorganism. In some embodiments, an inoculant (sometimes as microbial inoculant, or soil inoculant) is an agricultural amendment that uses beneficial microbes, such as PGPMs, (including, but not limited to endophytes) to promote plant health, growth and/or yield. Many of the microbes suitable for use in an inoculant form symbiotic relationships with the target crops where both parties benefit (mutualism).

As used herein, the phrases "associated with", "in association with", or "associated therewith" in reference to a microbial composition or strain/isolate described herein and a plant, plant part or plant seed refer to at least a juxtaposition or close proximity of the microbial composition or strain/isolate and the plant, plant part or plant seed. Such a juxtaposition can be achieved by contacting or applying a microbial composition or strain/isolate to the plant, plant part, or plant seed, such as by spraying or coating the plant, plant part, or plant seed with the microbial composition, by applying as a foliar application to one or more above-ground tissues of the plant, and/or by applying the microbial composition to the soil or growth medium at, near or surrounding the site where the plant, plant part or plant seed is planted, growing, or will be planted or grown. According to many embodiments, the microbial composition is applied as a coating to the outer surface of a plant part or plant seed, which can exist as a layer around most or all of the plant part or plant seed. According to other embodiments, the microbial composition can be applied as a foliar spray or as a soil drench or application at or near the base of a crop plant. According to some embodiments, the microbial composition can be applied at or near the site of a plant seed in (or on) the soil or ground before, simultaneously with, or after planting of the plant seed.

As used herein, a "plant part" refers to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts can be viable, nonviable, regenerable, and/or non-regenerable, and plant parts can in some cases be developed, regenerated and/or grown into a plant, as the case may be. A "propagule" can include any plant part that is capable of growing into an entire plant, and can include, for example, cuttings, rhizomes, and tubers, depending on the particular plant species. Plant parts that can be treated or associated with a microbial composition can further include other cultured plant tissues or propagation materials, such as somatic embryos and callus, which can be regenerated, developed or grown into a plant.

Multiple variables in a field or agricultural environment can affect the ability of microbes to provide a positive impact on yield and/or tolerance against drought. The present inventors have utilized agricultural field environments to test the ability of various microbial strains or isolates to improve yield of crop plants and/or increase drought tolerance. By testing the ability of these microbial strains or isolates to positively impact plant yield and/or increasing drought tolerance under outdoor field conditions, numerous variables that could impact yield and/or increasing drought tolerance and affect the interaction between the microbe and the plant, such as weather conditions and humidity, day length, soil chemistry, and the surrounding atmosphere and microbiome in the soil, can be taken into account to measure yield and/or increasing drought tolerance. Thus, the present inventors have sought to identify microbial strains or isolates that positively impact yield and/or increasing drought tolerance of crop plants more directly under outdoor agricultural field conditions. Furthermore, by testing these microbes in a wide range of geographies, microbial strains or isolates can be identified that impact yield and/or increasing drought tolerance across a variety of different geographical field locations and growth conditions.

Microorganism Identity and Uses Microorganisms can be identified using their 16S rRNA or ITS sequences (in the case of fungi) as denoted in the Examples below. The entire genome of the microorganisms can also be sequenced for strain identification.

In one embodiment, the present disclosure identified the microorganism to be *Flavobacterium hawaineses* nov sp. H492, *Bacillus megaterium* H491, *Pseudomonas protegens*

CL45A, *Enterobacter* sp. nov 638, *Bacillus safensis* R950, *Streptomyces* sp. R518, *Trichoderma* sp. S089, *Burkholderia megapolitana* O437, *Flavobacterium sacchrophilum* R129, *Ramularia* sp. R223, or *Streptomyces laurentii* R914.

Plants and plants grown from seeds treated or associated with a microbial composition, and/or plants treated with a microbial composition at any stage(s) of development, can have one or more improved plant yield and/or drought tolerance traits or characteristics. Such improved traits can include increased yield and/or drought tolerance. Such plants can have yield traits and/or drought tolerance that are improved or increased by at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 150%, 175%, 200%, 225%, 250%, 275%, 300% (or more) in comparison to a control plant that has not been treated with a microbial composition. According to some embodiments, the yield of such plants can be increased or improved on average by at least 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or 20 bushels per acre.

Methods of Production The microorganisms can be cultivated in nutrient medium using methods known in the art. The organisms can be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation can take place in suitable nutrient medium comprising carbon and nitrogen sources and inorganic salts, using procedures known in the art. Suitable media are available from commercial sources or can be prepared according to published compositions.

In an embodiment, cultures of microorganisms can be prepared for use in microbial compositions using any standard or known static drying or liquid fermentation techniques known in the art. Optimal conditions for the cultivation of microorganisms can depend upon the particular strain. A person skilled in the art would be able to determine the appropriate nutrients and conditions. The microorganisms can be grown in aerobic liquid cultures on media which contain sources of carbon, nitrogen, and inorganic salts that can be assimilated by the microorganism and supportive of efficient cell growth. Carbon sources can include hexoses, such as glucose, and other sources that are readily assimilated such as amino acids, can be used. Many inorganic and proteinaceous materials can be used as nitrogen sources in the growth process. Nitrogen sources can include amino acids and urea, as well as ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the salts capable of yielding calcium, zinc, iron, manganese, magnesium, copper, cobalt, potassium, sodium, molybdate, phosphate, sulfate, chloride, borate, and like ions.

Microbe Inhabitant In some embodiments, one or more microbial strains disclosed herein are established as endophytes on the plant, after being applied to the plant, plant part, or to the plant's surroundings. In some embodiments, one or more microbial strains are established as endophytes on the plant in the reproductive tissue, vegetative tissue, regenerative tissues, plant parts, and/or progeny thereof. In some embodiments, one or more microbial strains are established as endophytes in the seed offspring of the plant that is exposed to or treated with a microbial strain, isolate, culture, or composition as described herein. Some embodiments relate to a plant, plant part, or a seed that is infected with at least one microbial strain as described herein.

Compositions According to some embodiments, a microbial strain or isolate can be present in a composition at an amount or concentration ranging from about $1\times10^1$ to about $1\times10^{15}$ colony forming units (cfu) per gram or milliliter. For example, a microbial strain or isolate can be present in a composition at an amount or concentration of at least $1\times10^1$, at least $1\times10^2$, at least $1\times10^3$, at least $1\times10^4$, at least $1\times10^5$, at least $1\times10^6$, at least $1\times10^7$, at least $1\times10^8$, at least $1\times10^9$, at least $1\times10^{10}$, at least $1\times10^{11}$, at least $1\times10^{12}$, at least $1\times10^{13}$, at least $1\times10^{14}$, or at least $1\times10^{15}$ (or more) cfu per gram or milliliter of the composition. As used herein, the term "colony forming unit" or "cfu" refers to a microbial cell or spore capable of propagating on or in a suitable growth medium or substrate (e.g., a soil) when conditions (e.g., temperature, moisture, nutrient availability, pH, etc.) are favorable for germination and/or microbial growth.

Compositions can comprise whole broth cultures, liquid cultures, or suspensions of a strain from microorganism disclosed herein, as well as supernatants, filtrates or extracts obtained, or the supernatant, filtrate and/or extract or one or more metabolites or isolated compounds derived from one or more strains of the present disclosure or combinations of the foregoing which in particular have yield improving and/or drought tolerance activity.

Microbe Delivery and Application Methods Microbial stains, isolates or whole cell broth cultures thereof, or microbial compositions can be delivered through several means. In some embodiments, they are delivered by seed treatment, seed priming, seedling dip, soil application, foliar spray, fruit spray, hive insert, sucker treatment, sett treatment, and a multiple delivery system.

In some embodiments, the microbial strains, whole cell broth cultures thereof or compositions comprising the same, as described herein, can be delivered by direct exposure or contact with a plant seed. In some embodiments, the seed can be coated with a microbial strain (or an isolate or a culture thereof) or a composition thereof. Seed treatment with microbes can be effective against several plant diseases.

In some embodiments, the microbial strains, isolates, whole cell broth cultures or compositions, as described herein, can be delivered by direct exposure or contact with a plant seed during seed priming process. Priming with microbes can increase germination and improve seedling establishment. Such priming procedures can initiate the physiological process of germination, but prevents the emergence of plumule and radicle. It has been recognized that initiation of the physiological process helps in the establishment and proliferation of the microbes on the spermosphere.

In some embodiments, the microbial strains, isolates, whole cell broth cultures thereof or compositions comprising the same, as described herein, can be delivered by seedling dip. Plant pathogens often enter host plants through root. In some embodiments, protection of rhizosphere region by prior colonization with microbes prevents the establishment of a host-parasite relationship.

In some embodiments, the microbial strains, isolates, whole cell broth cultures or compositions, as described herein, can be delivered by direct application to soil. Soil is the repertoire of both beneficial and pathogenic microbes. In some embodiments, delivering PGPMs to soil can suppress the establishment of pathogenic microbes.

In some embodiments, the microbial strains, isolates, whole cell broth cultures or compositions, as described herein, can be delivered by foliar spray or fruit spray. In some embodiments, delivering microbes directly to plant foliage or fruit can suppress pathogenic microbes contributing to various foliar diseases or post-harvest diseases.

In some embodiments, the microbial strains, isolates, whole cell broth cultures or compositions are delivered by hive insert. Honey bees and bumble bees serve as a vector for the dispersal of biocontrol agents of diseases of flowering and fruit crops. In some embodiments, a dispenser can be attached to the hive and loaded with the PGPMs, optionally in combination with other desired agents.

In some embodiments, the microbial strains, isolates, whole cell broth cultures or compositions are delivered by sucker treatment or sett treatment. microbes can plant a vital role in the management of soilborne diseases of vegetatively propagated crops. The delivery of microbes varies depending upon the crop. For crops such as banana, microbes can be delivered through sucker treatment (e.g., sucker dipping). For crops such as sugarcane, microbes can be delivered through sett treatment (e.g., sett dipping).

In some embodiments, the microbial strains, isolates, whole cell broth cultures or compositions are delivered by a multiple delivery system comprising two or more of the delivery systems as described herein.

According to another aspect, compositions are provided comprising a plant, plant part, or plant seed having a microbial strain or isolate described herein associated with, or applied to, the plant, plant part, or plant seed.

According to embodiments described herein, a plant or crop plant that can be treated or associated with compositions or formulations can include a variety of monocotyledonous (monocot) and dicotyledonous (dicot) agricultural plants. Examples can include row or cereal crops, such as maize (corn), wheat, rice, barley, oat, sorghum, other cereals, soybean, cotton, canola, sugar beets, alfalfa, and vegetables. Further examples include: Amaranthaceae (e.g., chard, spinach, sugar beet, quinoa), Asteraceae (e.g., artichoke, asters, chamomile, chicory, chrysanthemums, dahlias, daisies, echinacea, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or Zoysia), millet, oats, ornamental grasses, rice, rye, sorghum, sugar cane, triticale, wheat and other cereal crops, Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, petunia, potato, tobacco, tomato), and Vitaceae (e.g., grape). Wheat plants further include varieties of winter and spring wheat, such as hard red winter wheat, soft red winter wheat, hard white winter wheat, soft white winter wheat, Durum wheat, and hard red spring wheat. Further provided is a plant part or plant seed taken or derived from any of the foregoing plants.

A plant, plant part or plant seed can be transgenic or non-transgenic and/or contain one or more genetic changes or mutations. A "plant" refers to a plant at any stage of development including an embryo, seedling, and mature plant whether grown or developed from a seed, regenerated from a cultured tissue, or propagated in any manner.

Compositions in some embodiments can comprise a modified microbial strain. As used herein, the term "modified microbial strain" refers to a microbial strain that is modified from a strain or isolate provided herein. Modified microbial strains can be produced by any suitable method(s), including, but not limited to, a killed or lysed microbe (by heat, by chemical, and/or by physical force); an induced mutation, including but not limited to a chemically induced mutation, to a polynucleotide within any genome of the strain or isolate;

an insertion or deletion of one or more nucleotides within any genome within the strain or isolate, or combinations thereof; an inversion of at least one segment of DNA within any genome within the strain or isolate; a rearrangement of any genome within the strain or isolate; a generalized or specific transduction of homozygous or heterozygous polynucleotide segments into any genome within the strain or isolate; an introduction of one or more phage into any genome of the strain or isolate; a transformation of any strain or isolate resulting in the introduction into the strain or isolate of stably and autonomously replicating extrachromosomal DNA; any change to any genome or to the total DNA composition within the strain or isolate as a result of conjugation with any different microbial strain; and any combination of the foregoing. The term "modified microbial strain" includes a strain or isolate with (a) one or more heterologous nucleotide sequences, (b) one or more non-naturally occurring copies of a nucleotide sequence isolated from nature (i.e., additional copies of a gene that naturally occurs in the microbial strain from which the modified microbial strain was derived), (c) a lack of one or more nucleotide sequences that would otherwise be present in the natural reference strain by, for example, deleting nucleotide sequence, and (d) added extrachromosomal DNA. In some embodiments, a "modified microbial strain" comprises a combination of two or more nucleotide sequences (e.g., two or more naturally occurring genes that do not naturally occur in the same microbial strain or isolate) or comprise a nucleotide sequence isolated from nature at a locus that is different from the natural locus.

A microbial composition in some embodiments can be applied to a plant or plant material, such as one or more plant parts or plant seeds, by any standard treatment methodology known in the art, including but not limited to those listed above and other standard or conventional methods, such as mixing in a container (e.g., a bottle or bag), mechanical application, tumbling, spraying, immersion, solid matrix priming, etc. Other conventional coating methods and machines, such as fluidized bed techniques, the roller mill method, rotostatic seed treaters, and drum coaters, can also be used. Any conventional active or inert material can be used for contacting seeds with a seed treatment composition, such as conventional film-coating materials including, but not limited to, water-based film coating materials. According to some embodiments, plant materials (e.g., plant parts or seeds) are coated by applying a composition described herein to the inside wall of a round container, adding the plant material, and rotating the container such that the material comes into contact with the composition, a process known in the art as "container coating". Continuous treatment systems, which are calibrated to apply a composition at a predefined rate in proportion to a continuous flow of material, such as plant seed, can also be employed.

Formulations According to embodiments of the present disclosure, compositions provided comprises various formulations of a microbial or bacterial strain. Such formulations can include various salts, fillers, binders, solvents, carriers, excipients, adjuvants, and/or other components or ingredients, such as further described below. The amount and concentration of each component in a composition of the present disclosure depend on many factors, such as the type, size and volume of material to which the composition will be applied, the type(s) of microorganisms in the composition, the number of microorganisms in the composition, the stability of the microorganisms in the composition, storage conditions (e.g., temperature, relative humidity, duration), etc. One skilled in the art would understand how to determine acceptable, effective and appropriate amounts and concentrations for various formulation components of microbial compositions of the present disclosure. In some embodiments, compositions of the present disclosure can comprise one or more carriers in an amount/concentration of about 0.1 to about 99.9% or more (by weight or volume based on the total weight or volume of the composition). For example, compositions of the present disclosure can comprise one or more carriers and/or other components in an amount or concentration of about 0.1, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99 or 99.5% or more (by weight or volume). The microbial strain or isolate can be present in a composition or formulation in any suitable form(s). According to some embodiments, the microbial strain or isolate can be a bacterial endophyte or a root or phylloplane colonizer. According to some embodiments, the microbial strain or isolate can be in the form of vegetative cells and/or spores. In addition, the microbes can be lysed or heat killed after fermentation.

According to some embodiments, compositions and formulations can comprise an "effective amount", "effective concentration", and/or "effective dosage" of a microbial strain or isolate to impart a positive trait or benefit to a crop plant, such as increased yield, drought stress tolerance, nutrient availability or uptake, or improved soil characteristics, when used in association with the crop plant. The effective amount/concentration/dosage of the microbial strain or isolate can depend on a number of factors, such as the type, size and volume of seeds or plant material to which the composition or formulation will be applied, the magnitude of the desired benefit, trait or effect, the stability of the microbe in the composition or formulation or when applied to a plant, plant part or plant seed, the identity and amounts of other ingredients in the composition or formulation, the manner of application to a seed, plant material, soil or growth medium, and the relevant storage conditions (e.g., temperature, relative humidity, duration of storage, lighting, etc.). Those skilled in the art can determine an effective amount/concentration/dosage using dose-response experiments or other known method.

Compositions of the present disclosure can further comprise an agriculturally acceptable carrier in combination with the microbial strain or isolate. As used herein, the term "agriculturally acceptable" in reference to a carrier, material, ingredient, or substance of a microbial composition comprising a microbial strain or isolate means that the carrier, material, ingredient or substance, as the case may be, (i) is compatible with other ingredients of the microbial composition at least for the purpose in which the microbial composition will be used, (ii) can be included in the microbial composition to effectively and viably deliver the microbial strain or isolate to a plant, plant part, plant seed, or plant growth medium (e.g., soil), (iii) is not normally associated with the microbial strain or isolate in nature (at least in the form in which it will be used), and (iv) is not deleterious to a plant, plant part, or plant seed to which the composition will be associated or applied (at least in the manner and amount in which it will be applied to, or associated with, the plant, plant part, or plant seed).

A "carrier" is defined as any substance or material that can be used and/or combined with a microbial strain or isolate to improve the delivery or effectiveness of the microbial strain or isolate to a plant, plant part or plant seed. An agriculturally acceptable carrier can include a soil-compatible carrier, a seed-compatible carrier, and/or a foliar-compatible carrier. As used herein, the term "soil-compatible carrier" refers to a material that can be added or applied to a soil without causing/having an unduly adverse effect on plant yield, soil structure, soil drainage, or the like. The term "seed-compatible carrier" refers to a material that can be added or applied to a seed without causing/having an unduly adverse effect on the seed, seed germination, the plant that grows from the seed, or the like. The term "foliar-compatible carrier" refers to a material that can be added or applied to an above ground portion of a plant or plant part without causing/having an unduly adverse effect on plant yield, plant health, or the like. Selection of appropriate carrier materials will depend on the intended application(s) and the microorganism(s) present in the composition. The carrier material(s) can be selected and/or combined to provide a composition or formulation in the form of a liquid, gel, slurry, or solid.

Compositions can comprise one or more liquid and/or gel carriers, and/or one or more aqueous and/or non-aqueous solvents. As used herein, the term "non-aqueous" can refer to a composition, solvent or substance that comprises no more than a trace amount of water (e.g., no more than 0.5% water by weight).

According to some embodiments, compositions can be in solid or powder form and/or comprise one or more solid carriers. For example, compositions can comprise one or more powders (e.g., wettable powders) and/or granules. Non-limiting examples of solid carriers that can be useful in compositions of the present disclosure include peat-based powders and granules, freeze-dried powders, spray-dried powders, and combinations thereof. Additional examples of carriers that can be included in compositions of the present disclosure can be found in Burges, H. D., Formulation of Microbial Biopesticides: Beneficial Microorganisms, Nematodes and Seed Treatments, Springer Science & Business Media (2012); and Inoue & Horikoshi, J. FERMENTATION BIOENG.71(3): 194 (1991), the contents and disclosures of which are incorporated herein by reference.

Compositions in some embodiments can be in liquid or gel form and/or comprise one or more liquid and/or gel carriers. Carriers in compositions or formulations can comprise a growth medium or broth suitable for culturing one or more of the microorganisms in the composition. For example, compositions can comprise a Czapek-Dox medium, a glycerol yeast extract, a mannitol yeast extract, a potato dextrose broth, and/or a YEM media. Commercial carriers can be used in accordance with a manufacturer's recommended amounts or concentrations.

Compositions can comprise one or more various solvents, such as organic, inorganic, non-aqueous and/or aqueous solvent(s). Examples of inorganic solvents include decane, dodecane, hexylether, and nonane. Examples of commercially available organic solvents include pentadecane, ISOPAR M, ISOPAR V, and ISOPAR L (Exxon Mobil). Additional examples of solvents that can be included in compositions and formulations can be found in Burges, supra; Inoue & Horikoshi, supra, the contents and disclosures of which are incorporated herein by reference. According to some embodiments, an aqueous solvent, such as water, can be combined with a co-solvent, such as ethyl lactate, methyl soyate/ethyl lactate co-solvent blends (e.g., STEPOSOL, available from Stepan), isopropanol, acetone, 1,2-propanediol, n-alkylpyrrolidones (e.g., the AGSOLEX series, available from ISP), a petroleum based-oil (e.g., AROMATIC series and SOLVES SO series available from Exxon Mobil), isoparaffinic fluids (e.g., ISOPAR series, available from Exxon Mobil), cycloparaffinic fluids (e.g., NAPPAR 6, available from Exxon Mobil), mineral spirits (e.g., VARSOL series available from Exxon Mobil), and mineral oils (e.g., paraffin oil). According to some embodiments, compositions can comprise one or more co-solvent(s) in addition to an aqueous solvent or water. Such co-solvents) can include, for example, non-aqueous solvents, such as one or more the foregoing non-aqueous solvents.

According to some embodiments, compositions including formulations can have a desired pH in a range from about 4.5 to about 9.5. Compositions of the present disclosure can comprise any suitable pH buffer(s) known in the art. For example, compositions can have a pH in a range from about 6 to about 8, or a pH of about 5, 5.5, 6, 6.5, 7, 7.5, 8 or 8.5. To maintain a desired pH, a composition can comprise one or more bufferes in a buffer solution. pH buffers can be selected to provide an aqueous composition having a pH of less than 10, typically from about 4.5 to about 9.5, from about 6 to about 8, or about 7. Buffer solutions suitable for a variety of pH ranges are known in the art.

Compositions can comprise one or more thickeners, rheology modifying agents, or stabilizing agents ("stabilizers"). Examples of stabilizers include anionic polysaccharides and cellulose derivatives. A stabilizer can comprise, for example, a clay, a silica, or a colloidal hydrophilic silica. Non-limiting examples of commercially available stabilizers include KELZAN CC (Kelco), methyl cellulose, carboxymethylcellulose and 2-hydroxyethylcellulose, hydroxymethylcellulose, kaolin, maltodextrin, malt extract, microcrystalline cellulose, and hygroscopic polymers. A non-limiting example of a commercially available colloidal hydrophilic silica is AEROSIL (Evonik). A stabilizer can also include a monosaccharide, disaccharide or sugar alcohol, such as maltose, trehalose, lactose, sucrose, cellobiose, mannitol, xylitol, or sorbitol, and any combination thereof. A stabilizer component can comprise from about 0.05% to about 10% by weight of a composition. For example, a stabilizer component can comprise from about 0.1% to about 5%, from about 0.1% to about 2%, or from about 0.1% to about 1% by weight of a composition.

Compositions of the present disclosure can comprise any suitable anti-settling agent(s), including, but not limited to, polyvinyl acetate, polyvinyl alcohols with different degrees of hydrolysis, polyvinylpyrrolidones, polyacrylates, acrylate-, polyol- or polyester-based paint system binders, which are soluble or dispersible in water, co-polymers of two or more monomers, such as acrylic acid, methacrylic acid, itaconic acid, maleic acid, fumaric acid, maleic anhydride, vinylpyrrolidone, ethylenically unsaturated monomers, such as ethylene, butadiene, isoprene, chloroprene, styrene, divinylbenzene, ot-methylstyrene or p-methylstyrene, vinyl halides, such as vinyl chloride and vinylidene chloride, vinyl esters, such as vinyl acetate, vinyl propionate or vinyl stearate, vinyl methyl ketones or esters of acrylic acid or methacrylic acid with monohydric alcohols or polyols, such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, diethyl esters or monoesters of unsaturated dicarboxylic acids, (meth)acrylamido-N-methylol methyl ether, amides or nitriles, such as acrylamide, methacrylamide, N-methylol(meth)acrylamide, acrylonitrile, methacrylonitrile, N-substituted maleiraides, and ethers, such as vinyl butyl ether, vinyl isobutyl ether or vinyl phenyl ether, and any combinations thereof.

Compositions in some embodiments can comprise one or more oxidation control components, which can include one or more antioxidants (e.g., one or more of: ascorbic acid, ascorbyl palmitate, ascorbyl stearate, calcium ascorbate, carotenoids, lipoic acid, phenolic compounds (e.g., one or more flavonoids, flavones and/or flavonols), potassium ascorbate, sodium ascorbate, one or more thiols (e.g., glutathione, lipoic acid and/or N-acetyl cysteine), tocopherols, one or more tocotrienols, ubiquinone and/or uric acid) and/or one or more oxygen scavengers, such as ascorbic acid and/or sodium hydrogen carbonate.

Composition in some embodiments can comprise one or more UV protectants, such as one or more aromatic amino acids (e.g., tryptophan, tyrosine), carotenoids, cinnamates, lignosulfonates (e.g., calcium lignosulfonate, sodium ligno sulfonate), melanins, mycosporines, polyphenols and/or salicylates). Non-limiting examples of UV protectants include Borregaard LignoTech™ lignosulfonates (e.g., Borresperse 3 A, Borresperse CA, Borresperse NA, Marasperse AG, Norlig A, Norlig 11D, Ufoxane 3 A, Ultrazine NA, Vanisperse CB; Borregaard Lignotech, Sarpsborg, Norway) and combinations thereof. See, for example, BURGES, FORMULATION OF MICROBIAL BIOPESTICIDES: BENEFICIAL MICROORGANISMS, NEMATODES AND SEED TREATMENTS (Springer Science & Business Media) (2012).

Compositions in some embodiments can comprise one or more agriculturally acceptable polymers, such as agar, alginate, carrageenan, cellulose, guar gum, locust bean gum, methylcellulose, pectin, polycaprolactone, polylactide, polyvinyl alcohol, polyvinyl pyrrolidone, sodium carboxymethyl cellulose, starch and/or xanthan gum. In an aspect, the one or more polymers is a natural polymer (e.g., agar, starch, alginate, pectin, cellulose, etc.), a synthetic polymer, a biodegradable polymer (e.g., polycaprolactone, polylactide, polyvinyl alcohol, etc.), or a combination thereof. For a non-limiting list of polymers useful for the compositions described herein, see, e.g., Pouci et ah, Am. J. Agri. & Biol. Sci., 3(1):299-314 (2008), the content and disclosure of which are incorporated herein by reference.

Compositions in some embodiments can comprise one or more agriculturally acceptable dispersants, which can include one or more surfactants and/or wetting agents. Dispersants can be used to maintain a homogeneous or even distribution of particles or cells in a suspension, such as an even or homogeneous distribution of a microbial strain or isolate, which can be used for solid or dried formulations of a microbe and/or liquid formulations or fermentates. In addition to maintaining an even distribution of the microbe in a final composition or formulation and during application of a composition or formulation to a plant, plant part or plant seed, a dispersant or wetting agent can also facilitate mixing of a microbe with other ingredients and solvents of a microbial formulation or composition and avoid aggregation or clumping of particles, or their adherence to container walls, etc., during formulation of a microbial composition. A dispersant can reduce the cohesiveness of like particles, the surface tension of a liquid, the interfacial tension between two liquids, and/or the interfacial tension between or a liquid and a solid. Compositions can comprise a primary dispersant in combination with one or more secondary dispersants, and the primary and secondary dispersants can be different types (e.g., non-ionic, cationic, anionic, and/or zwitterionic). Wetting agents can be used with compositions applied to soils, particularly hydrophobic soils, to improve the infiltration and/or penetration of water into a soil. The wetting agent or dispersant can be an adjuvant, oil, surfactant, buffer, acidifier, or combination thereof. The wetting agent or dispersant can be a surfactant, such as one or more non-ionic surfactants, one or more cationic surfactants, one or more anionic surfactants, one or more zwitterionic surfactants, or any combination thereof.

Non-liming examples of anionic surfactants include one or more alkyl carboxylates (e.g., sodium stearate), alcohol ether carboxylates, phenol ether carboxylates, alkyl sulfates (e.g., alkyl lauryl sulfate and/or sodium lauryl sulfate), alkyl ether sulfates, alcohol sulfates, alcohol ether sulfates, alkyl amido ether sulfates, alkyl aryl ether sulfates, alkyl aryl polyether sulfates, alkyl aryl sulfates, alkyl aryl sulfonates, alkyl sulfonates, alkyl amide sulfonates, aryl sulfonates, alkyl benzene sulfonates, alkyl diphenyloxide sulfonate, alpha-olefin sulfonates, alkyl naphthalene sulfonates, paraffin sulfonates, sulfosuccinates, alkyl sulfosuccinates, alkyl ether sulfosuccinates, alkylamide sulfosuccinates, mono- or disulfosuccinate esters of alcohols or polyalkoxylated alkanols, alkyl sulfosuccinamate, alkyl sulfoacetates, alkyl phosphates, alkyl ether phosphates, mono- or diphosphate esters of polyalkoxylated alkyl alcohols or alkyl phenols, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, toluene sulfonates and/or xylene sulfonates), ionic surfactants (e.g., one or more ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty esters, sorbitan fatty acid alcohol ethoxylates and/orsorbitan fatty acid ester ethoxylates), nonionic surfactants (e.g., one or more alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers (e.g.,), glycerol esters, glycol alkyl ethers (e.g., polyoxyethylene glycol alkyl ethers, polyoxypropylene glycol alkyl ethers,), glycol alkylphenol ethers (e.g., polyoxyethylene glycol alkylphenol ethers,), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers (e.g., Triton X-100), polyvinyl pynolidones, sugar-based alkyl polyglycosides, sulfoanylamides, sorbitan fatty acid alcohol ethoxylates, sorbitan fatty acid ester ethoxylates, sorbitan fatty acid esters, tertiary acetylenic glycols and/or TWEEN 80), styrene acrylic polymers, modified styrene acrylic polymers and/or zwitterionic surfactants (e.g., 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins. Anionic surfactants can be either water soluble anionic surfactants, water insoluble anionic surfactants, or a combination of water soluble anionic surfactants and water insoluble anionic surfactants.

Other non-limiting examples of commercially available anionic surfactants include sodium dodecylsulfate (Na-DS, SDS), MORWET D-425 (a sodium salt of alkyl naphthalene sulfonate condensate, available from Akzo Nobel), MORWET D-500 (a sodium salt of alkyl naphthalene sulfonate condensate with a block copolymer, available from Akzo Nobel), sodium dodecylbenzene sulfonic acid (Na-DBSA) (Aldrich), diphenyloxide disulfonate, naphthalene formaldehyde condensate, DOWFAX (Dow), dihexylsulfosuccinate, and dioctylsulfosuccinate, TWEEN®, alkyl naphthalene sulfonate condensates, and salts thereof.

Seed Coating The composition disclosed herein can be formulated into a seed coating material. Seed coating methods and compositions that are known in the art can be used when they are modified by the addition of one of the compositions disclosed herein. Such coating methods and apparatus for their application are disclosed in, for example but not limited to, U.S. Pat. Nos. 5,918,413; 5,554,445; 5,389,399; 4,759,945; and 4,465,017. Seed coating compositions are disclosed, for example, in U.S. Pat. Appl. No. US20100154299, U.S. Pat. Nos. 5,939,356; 5,876,739, 5,849,320; 5,791,084, 5,661,103; 5,580,544, 5,328,942; 4,735,015; 4,634,587; 4,372,080, 4,339,456; and 4,245,432, which are all incorporated herein by reference.

In brief, A variety of additives can be added to the seed treatment formulations comprising the compositions disclosed herein. Binders can be added and include those composed preferably of an adhesive polymer that can be natural or synthetic without phytotoxic effect on the seed to be coated. The binder can be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arables; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

In some specific embodiments, in addition to the microbial cells or spores, the coating can further comprise a layer of adherent. The adherent should be non-toxic, biodegradable, and adhesive. Examples of such materials include, but are not limited to, polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrans; alginates; sugars; molasses; polyvinyl pyrrolidones; polysaccharides; proteins; fats; oils; gum arables; gelatins; syrups; and starches. More examples can be found in, for example, U.S. Pat. No. 7,213,367 and U.S. Pat. Appin. No. US20100189693, incorporated herein by reference.

Various additives, such as adherents, dispersants, surfactants, and nutrient and buffer ingredients, can also be included in the seed treatment formulation. Other seed treatment additives include, but are not limited to, coating agents, wetting agents, buffering agents, and polysaccharides. At least one agriculturally acceptable carrier can be added to the seed treatment formulation such as water, solids or dry powders. The dry powders can be derived from a variety of materials such as calcium carbonate, gypsum, vermiculite, talc, humus, activated charcoal, and various phosphorous compounds.

In some embodiments, the seed coating composition can comprise at least one filler which is an organic or inorganic, natural or synthetic component with which the active components are combined to facilitate its application onto the seed. In certain embodiments, the filler is an inert solid such as clays, natural or synthetic silicates, silica, resins, waxes, solid fertilizers (for example, ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminum or magnesium silicates.

The seed treatment formulation can further include one or more of the following ingredients: other pesticides, including compounds that act only below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; chemical fertilizers; biological fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi. These ingredients can be added as a separate layer on the seed or alternatively, can be added as part of the seed coating composition of the embodiments.

Additional Substances In addition to a microbial strain or isolate or whole cell broth culture described herein, compositions and formulations can further comprise one or more pesticidal agents. Pesticidal agents include chemical pesticides and biopesticides or biocontrol agents. Various types of chemical pesticides include acaricides, insecticides, nematicides, fungicides, gastropodicides, herbicides, virucides, bactericides, and combinations thereof. Biopesticides or biocontrol agents can include bacteria, fungi, beneficial nematodes, and viruses that exhibit pesticidal activity. Compositions can comprise other agents for pest control, such as microbial extracts, plant growth activators, and/or plant defense agents.

Compositions in some embodiments can comprise one or more chemical acaricides, insecticides, and/or nematicides. Non-limiting examples of chemical acaricides, insecticides, and/or nematicides can include one or more carbamates, diamides, macrocyclic lactones, neonicotinoids, organophosphates, phenylpyrazoles, pyrethrins, spinosyns, synthetic pyrethroids, tetronic acids and/or tetramic acids. Non-limiting examples of chemical acaricides, insecticides and nematicides that can be useful in compositions of the present disclosure include abamectin, acrinathrin, aldicarb, aldoxycarb, alpha-cypermethrin, betacyfluthrin, bifenthrin, cyhalothrin, cypermethrin, deltamethrin, csfenvalcrate, etofenprox, fenpropathrin, fenvalerate, flucythrinate, fosthiazate, lambda-cyhalothrin, gamma-cyhalothrin, permethrin, tau-fluvalinate, transfluthrin, zeta-cypermethrin, cyfluthrin, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (e.g., Rynaxypyr), cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino}furan-2(5H)-one, 3,5-disubstituted-1,2,4-oxadiazole compounds, 3-phenyl-5-(thien-2-yl)-1,2,4-oxadiazole, cadusaphos, carbaryl, carbofuran, ethoprophos, thiodicarb, aldicarb, aldoxycarb, metamidophos, methiocarb, sulfoxaflor, methamidophos, cyantraniliprole and tioxazofen and any combinations thereof. Additional non-limiting examples of chemical acaricides, insecticides, and/or nematicides can include one or more of abamectin, aldicarb, aldoxycarb, bifenthrin, carbofuran, chlorantraniliporle, chlothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam and/or thiodicarb, and any combinations thereof.

Additional non-limiting examples of acaricides, insecticides and nematicides that can be included or used in compositions can be found in Steffey and Gray, Managing Insect Pests, ILLINOIS AGRONOMY HANDBOOK (2008); and Niblack, Nematodes, ILLINOIS AGRONOMY HANDBOOK (2008), the contents and disclosures of which are incorporated herein by reference. Non-limiting examples of commercial insecticides which can be suitable for the compositions disclosed herein include CRUISER (Syngenta, Wilmington, Del.), GAUCHO and PONCHO (Gustafson, Piano, Tex.). Active ingredients in these and other commercial insecticides can include thiamethoxam, clothianidin, and imidacloprid. Commercial acaricides, insecticides, and/or nematicides can be used in accordance with a manufacturer's recommended amounts or concentrations.

According to some embodiments, compositions can also comprise one or more biopesticidal microorganisms, the presence and/or output of which is toxic to an acarid, insect and/or nematode. For example, compositions can comprise one or more of *Bacillus firmus* 1-1582, *Bacillus mycoides* AQ726, NRRL B-21664; *Beauveria bassiana* ATCC-74040, *Beauveria bassiana* ATCC-74250, *Burkholderia* sp. A396 sp. nov. *rinojensis*, NRRL B-50319, *Chromobacterium sub-tsugae*NRRL B-30655, *Chromobacterium vaccinii* NRRL B-50880, *Flavobacterium* H492, NRRL B-50584, *Metarhizium anisopliae* F52 (also known as *Metarhizium anisopliae* strain 52, *Metarhizium anisopliae* strain 7, *Metarhizium anisopliae* strain 43, and/or *Metarhizium anisopliae* BIO-1020, TAE-001; deposited as DSM 3884, DSM 3885, ATCC 90448, SD 170 and ARSEF 7711), *Paecilomyces fumosoroseus* FE991, and any combinations thereof.

Compositions in some embodiments can comprise one or more chemical fungicides. Non-limiting examples of chemical fungicides include one or more: aromatic hydrocarbons, benzthiadiazole, carboxylic acid amides, morpholines, phenylamides, phosphonates, thiazolidines, thiophene, quinone outside inhibitors and strobilurins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester, and 2-(2-(3-(2,6-dichlorophenyl)-1-methyl-allylideneaminooxymethyl)-phenyl)-2-methoxy-imino-N-methyl-acetamide, carboxamides, such as carboxanilides (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthio-biphenyl-2-yl)-3-difluoromethyl-1-methyl-1H-pyra-zole-4-carboxamide, N-(2-(1,3,3-trimethylbutyl)-phenyl)-1,3-dimethyl-5-fluoro-1H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, mandiproamid, fenehexamid, oxytetracyclin, silthiofam, and N-(6-methoxy-pyridin-3-yl) cyclopropanecarboxylic acid amide, spiroxamine, azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles (e.g., cyazofamid, imazalil, pefurazoate, prochloraz, triflumizol); heterocyclic compounds, such as pyridines (e.g., fluazinam, pyrifenox (cf.Dlb), 3[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines (e.g., aldimorph, dodemorph, dodemorph-acetate, fenpropimorph, tridemorph), piperidines (e.g., fenpropidin); dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydro-pyrazole-1-carbothioic acid 5-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a] pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A), nitrophenyl derivates (e.g., binapacryl, dicloran, dinobuton, dinocap, nitrothal-isopropyl, tecnazen). organometal compounds (e.g., fentin salts, such as fentinacetate, fentin chloride, fentin hydroxide); sulfur-containing heterocyclyl compounds (e.g., dithianon, isoprothiolane), organophosphorus compounds (e.g., edifenphos, fosetyl, iprobenfos, phosphorus acid and its salts, pyrazophos, tolclofos-methyl), organochlorine compounds (e.g., chlorothalonil, dichlofluanid, dichlorophen, flusulfamide, hexachlorobenzene, pencycuron, pentachlorphenole and its salts, phthalide, quintozene, thiophanate-methyl, thiophanates, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In an aspect, compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-A1, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole, and any combinations thereof.

Compositions in some embodiments can comprise one or more chemical herbicides. The herbicides can be a pre-emergent herbicide, a post-emergent herbicide, or a combination thereof. Non-limiting examples of chemical herbicides can comprise one or more acetyl CoA carboxylase (ACCase) inhibitors, acetolactate synthase (ALS) inhibitors, acetanilides, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate synthase (EPSPS) inhibitors, glutamine synthetase inhibitors, dihydropteroate synthetase inhibitors, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors and/or one or more salts, esters, racemic mixtures and/or resolved isomers thereof. Non-limiting examples of chemical herbicides that can be useful in compositions of the present disclosure include 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluro, clethodim, clodinafop, clomazone, cyanazine, cycloxydim, cyhalofop, desmedipham, desmetryn, dicamba, diclofop, dimefuron, diflufenican, diuron, dithiopyr, ethofumesate, fenoxaprop, foramsulfron, fluazifop, fluazifop-P, flufenacet, fluometuron, flufenpyr-ethyl, flumiclorac, flumiclorac-pentyl, flumioxazin, fluoroglycofen, fluthiacet-methyl, fomesafen, fomesafen, glyphosate, glufosinate, halosulfuron, haloxyfop, hexazinone, iodosulfuron, indaziflam, imazamox, imazaquin, imazethapyr, ioxynil, isoproturon, isoxaflutole, lactofen, linuron, mecoprop, mecoprop-P, mesosulfuron, mesotrion, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometry, propachlor, propanil, propaquizafop, propisochlor, propoxycarbazone, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thaxtomin (e.g., the thaxtomins described in U.S. Pat. No. 7,989,393), thiencarbazone-methyl, thenylchlor, tralkoxydim, triclopyr, trietazine, trifloxysulfuron, tropramezone, salts and esters thereof; racemic mixtures and resolved isomers thereof and combinations thereof. In an aspect, compositions of the present disclosure comprise acetochlor, clethodim, dicamba, flumioxazin, fomesafen, glyphosate, glufosinate, mesotrione, quizalofop, saflufenacil, sulcotrione, S-3100 and/or 2,4-D, and combinations thereof. Additional examples of herbicides that can be included in compositions in some embodiments can be found in Hager, Weed Management, Illinois Agronomy Handbook (2008); and Loux et ah, Weed Control Guide for Ohio, Indiana and Illinois (2015), the contents and disclosures of which are incorporated herein by reference. Commercial herbicides can be used in accordance with a manufacturer's recommended amounts or concentrations.

In addition to a microbial strain or isolate of the present disclosure, compositions and formulations can further comprise one or more agriculturally beneficial agents, such as bio stimulants, nutrients, plant signal molecules, or biologically active agents.

Compositions in some embodiments can comprise one or more biologically active ingredients. Non-limiting examples of biologically active ingredients include plant growth regulators, plant signal molecules, growth enhancers, microbial stimulating molecules, biomolecules, soil amendments, nutrients, plant nutrient enhancers, etc., such as iipo-chitooligosaccharides (LCO), chitooligosaccharides (CO), chitinous compounds, flavonoids, jasmonic acid or derivatives thereof (e.g., jasmonates), cytokinins, auxins, gibberellins, absiscic acid, ethylene, brassinosteroids, salicylates, macro- and micro-nutrients, linoleic acid or derivatives thereof, linolenic acid or derivatives thereof, karrikins, etc.) and beneficial microorganisms including various bacterial and/or fungal strains (e.g., *Rhizobium* spp., *Brady rhizobium* spp., *Sinorhizobium* spp., *Azorhizohium* spp., *Glomus* spp., *Gigaspora* spp., *Hymenoscyphous* spp., *Oidiodendron* spp., *Laccaria* spp., *Pisoliths* spp., *Rhizopogon* spp., *Scleroderma* spp., *Rhizoctonia* spp., *Acinetobacter* spp., *Arthrobacter* spp, *Arthroboirys* spp., *Aspergillus* spp., *Azospirillum* spp, *Bacillus* spp, *Burkholderia* spp., *Candida* spp., *Chryseomonas* spp., *Enterobacter* spp., *Eupenicillium* spp., *Exiguobacterium*. spp., *Klebsiella* spp., *Kluyvera* spp., *Microbacterium* spp., *Mucor* spp., *Paecilomyces* spp., *PaenibaciUus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., etc.), and combinations thereof.

EXAMPLES

Example 1. Isolation and Identification of the Microbes

The following strains disclosed herein are identified as either plant yield enhancer and/or drought tolerance promoter: *Flavobacterium hawaineses* nov sp. H492; *Bacillus megaterium* H491; *Pseudomonas protegens* (previously fluorescens) CL45A; *Enterobacter* sp. nov 638; *Bacillus safensis* R950; *Streptomyces* sp. R518; *Trichoderma* sp. S089; *Burkholderia megapolitana* O437; *Flavobacterium sacchrophilum* R129; *Ramularia* sp. R223; and *Streptomyces laurentii* R914. The strains were collected from various geographies and time. In order to identify them, 16S rRNA or ITS sequencing were carried out.

16S rRNA or ITS sequencing Once microbes were collected, their 16S rRNA were sequenced in order to identify the strain name. 16S rRNA sequencing is known in the art. Briefly, microbial isolates were streaked on fresh potato dextrose plates and allowed to grow for 1-3 days or until enough biomass was evident. A loopfull of the bacterium was resuspended in DNA extraction buffer (included in the MoBio kit) using a sterile loop. DNA was extracted using the MoBio Ultra Clean Microbial DNA extraction kit using the manufacturer's protocol. DNA extract was checked for quality and quantity by running a 5 uL aliquot on a 1% agarose gel.

PCR reactions for the amplification of the 16s rRNA gene were performed by combining a colony of MBI 401 with 20 uL nuclease-free sterile water, 25 uL GoTaq Green Mastermix, 1.5 uL forward primer, and 1.5 uL reverse primer. The PCR reaction was performed using a thermocycler PCR machine under the following conditions: 10 minutes at 95° C. (initial denaturing), 30 cycles of 45 seconds at 94° C., 45 seconds at 55° C. and 2 minutes at 72° C., followed by 5 minutes at 72° C. (final extension) and a final hold temperature of 10° C. The size, quality and quantity of the PCR product was evaluated by running a 5 uL aliquot on a 1% agarose gel, and comparing the product band to a mass ladder.

Excess primers, nucleotides, enzyme and template were removed from the PCR product using the MoBio PCR clean up Kit following the manufacturer's instructions. The cleaned PCR product was subjected to direct sequencing using the primers described above. The forward and reverse sequences were aligned using the BioEdit software. The 16s rRNA gene consensus sequence of each microbe isolate was compared to those available sequences of representatives of the bacterial domain using NCBI BLAST. Strains with 100% sequence identity reveals some of the strains were already known in the art. The result is summarized in Table 1.

TABLE 1

| Microbe alternative name | Identification | Isolation Date | Origin |
| --- | --- | --- | --- |
| H492 or (MBI-302) | *Flavobacterium hawainensis* nov. sp. H492 | Feb. 1, 2010 | USA (NRRL B-50584) |
| H492 or (MBI-508) | *Bacillus megaterium* H491 | Feb. 1, 2010 | NRRL B-50769 |

TABLE 1-continued

| Microbe alternative name | Identification | Isolation Date | Origin |
|---|---|---|---|
| MBI-401 | *Pseudomonas protegens* CL45A | Jul. 10, 1996 (ATCC deposit) | ATCC 55799 |
| MBI-506 | *Enterobacter* sp. nov 638 | Mar. 4, 2011 (ATCC deposit) | PTA-11727 USA |
| O437 | *Burkholderia megapolitana* | Nov. 4, 2011 | USA |
| R129 | *Flavobacterium sacchrophilum* | Oct. 10, 2012 | USA |
| R223 | *Ramularia* sp. | Jan. 1, 2012 | Botswana, Africa |
| R518 | *Streptomyces* sp. | Dec. 27, 2012 | USA |
| R914 | *Streptomyces laurentii* | Mar. 7, 2013 | Thailand |
| R950 | *Bacillus safensis* | Mar. 4, 2013 | Thailand |
| S089 | *Trichoderma* sp. | Unknown | ... |

```
Flavobacterium hawainensis nov. sp H492
(MBI-302) 16S sequence:
                                      (SEQ ID No. 1)
GCTTACCATGCAGTCGAGGGGTAGAATTCTTCGGA

ATTTGAGACCGGCGCACGGGTGCGTAACGCGTATG

CAATCTGCCTTTCACAGAGGGATAGCCCAGAGAAA

TTTGGATTAATACCTCATAGTATTATGGAGTGGCA

TCACTTTATAATTAAAGTCACAACGGTGAAAGATG

AGCATGCGTCCCATTAGCTAGTTGGTAAGGTAACG

GCTTACCAAGGCGACGATGGGTAGGGGTCCTGAGA

GGGAGATCCCCCACACTGGTACTGAGACACGGACC

AGACTTATACGGGAGGCAGCAGTGAGGAATATTGG

TCAATGGACGCAAGTCTGAACCAGCCATGCCGCGT

GCAGGATGACGGTCCTATGGATTGTAAACTGCTTT

TGTACGAGAAGAAACACCTCTACGTGTAGAGACTT

GACGGTATCGTAAGAATAAGGATCGGCTAACTCCG

TGCCAGCAGCCGCGGTAATACGGAGGATCCAAGCG

TTATCCGGAATCATTGGGTTTAAAGGGTCTGTAGG

CGGTCTAGTAAGTCAGTGGTGAAAGCCCATCGCTC

AACGGTGGAACGGCCATTGATACTGCTGGACTTGA

ATTATTAGGAAGTAACTAGAATATGTAGTGTAGCG

GTGAAATGCTTAGAGATTACATGGAATACCAATTG

CGAAGGCAGGTTACTACTAATGGATTGACGCTGAT

GGACGAAAGCGTGGGTAGCGAACAGGATTAGATAC

CCTGGTAGTCCACGCCGTAAACGATGGATACTAGC

TGTTGGGCGCAAGTTCAGTGGCTAAGCGAAAGTGA

TAAGTATCCCACCTGGGGAGTACGGGCGCAAGCCT

GAAACTCAAAGGAATTGACGGGGGCCCGCACAAGC

GGTGGAGCATGTGGTTTAATTCGATGATACGCGAG

GAACCTTACCAAGGCTTAAATGTAGTTTGACCGAT

TTGGAAACAGATCTTTCGCAAGACAAATTACAAGG

TGCTGCATGGTTGTCGTCAGCTCGTGCCGTGAGGT

GTCAGGTTAAGTCCTATAACGAGCGCAACCCCTGT

TGTTAGTTGCCAGCGATTCGGTCGGGAACTCTAAC

AAGACTGCCAGTGCAAACTGTGAGGAAGGTGGGGA

TGACGTCAAATCATCACGGCCCTTACGCCTTGGGC

TACACACGTGCTACAATGGCCGGTACAGAGAGCAG

CCACCTCGCGAGGGGGAGCGAATCTATAAAGCCGG

TCACAGTTCGGATCGGAGTCTGCAACTCGACTCCG

TGAAGCTGGAATCGCTAGTAATCGGATATCAGCCA

TGATCCGGTGAATACGTTCCCGGGCCTTGTACACA

CCGCCCGTCAAGCCATGGAAGCTGGGGGTGCCTGA

AGTCGGTGACCGCAAGGAGCTGCCTAGGGTAAAAC

TGGTAACTAGGGCTAA.

Bacillus megaterium H491 (MBI 508)
16S sequence:
                                      (SEQ ID No. 2)
GACGGAGCAACGCCGCGTGAGTGATGAAGGCTTTC

GGGTCGTAAAACTCTGTTGTTAGGGAAGAACAAGT

ACAAGAGTAACTGCTTGTACCTTGACGGTACCTAA

CCAGAAAGCCACGGCTAACTACGTGCCAGCAGCCG

CGGTAATACGTAGGTGGCAAGCGTTATCCGGAATT

ATTGGGCGTAAAGCGCGCGCAGGCGGTTTCTTAAG

TCTGATGTGAAAGCCCACGGCTCAACCGTGGAGGG

TCATTGGAAACTGGGGAACTTGAGTGCAGAAGAGA

AAAGCGGAATTCCACGTGTAGCGGTGAAATGCGTA

GAGATGTGGAGGAACACCAGTGGCGAAGGCGGCTT

TTTGGTCTGTAACTGACGCTGAGGCGCGAAAGCGT

GGGGAGCAAACAGGATTAGATACCCTGGTAGTCCA

CGCCGTAAACGATGAGTGCTAAGTGTTAGAGGGTT

TCCGCCCTTTAGTGCTGCAGCTAACGCATTAAGCA

CTCCGCCTGGGGAGTACGGTCGCAAGACTGAAACT

CAAAGGAATTGACGGGGGCCCGCACAAGCGGTGGA
```

GCATGTGGTTTAATTCGAAGCAACGCGAAGAACCT
TACCAGGTCTTGACATCCTCTGACAACTCTAGAGA
TAGAGCGTTCCCCTTCGGGGGACAGAGTGACAGGT
GGTGCATGGTTGTCGTCAGCTCGTGTCGTGAGATG
TTGGGTTAAGTCCCGCAACGAGCGCAACCCTTGAT
CTTAGTTGCCAGCATTCAGTTGGGCACTCTAAGGT
GACTGCCGGTGACAAACCGGAGGAAGGTGGGGATG
ACGTCAAATCATCATGCCCCTTATGACCTGGGCTA
CACACGTGCTACAATGGATGGTACAAAGGGCTGCA
AGACCGCGAGGTCAAGCCAATCCCATAAAACCATT
CTCAGTTCGGATTGTAGGCTGCAACTCGCCTACAT
GAAGCTGGAATCGCTAGTAATCGCGGATCAGCATG
CCGCGGTGAATACGTTCCCGGGCCTTGTACACACC
GCCCGTCACACCACGAGAGTTTGTAACACCCGAAG
TCGGTGGAGTAACCGTAAGGAGCTAGCCGCCTAAG
GTGGGACAGATGATTGGGTGAAGTCGTAACAAGG
TAGCCGTATCGGAAGGTGCGGCTGGATCACCTCCT
TTCTA.

Pseudomonas protegens CL45A (MBI-401)
16S sequence:
                                (SEQ ID No. 3)
CATGCAAGTCGAGCGGCAGCACGGGTACTTGTACC
TGGTGGCGAGCGGCGGACGGGTGAGTAATGCCTAG
GAATCTGCCTAGTAGTGGGGGATAACGTCCGGAAA
CGGGCGCTAATACCGCATACGTCCTACGGGAGAAA
GTGGGGGATCTTCGGACCTCACGCTATTAGATGAG
CCTAGGTCGGATTAGCTAGTTGGTGAGGTAATGGC
TCACCAAGGCGACGATCCGTAACTGGTCTGAGAGG
ATGATCAGTCACACTGGAACTGAGACACGGTCCAG
AMTCCTACGGGAGGCAGCAGTGGGGAATATTGGAC
AATGGGCGAAAGCCTGATCCAGCCATGCCGCGTGT
GTGAAGAAGGTCTTCGGATTGTAAAGCACTTTAAG
TTGGGAGGAAGGGCAGTTACCTAATACGTGATTGT
TTTGACGTTACCGACAGAATAAGCACCGGCTAAC
TCTGTGCCCAGCAGCCGCGGTAATACAGAGGGTGC
AAGCGTTAATCGGAATTACTGGGCGTAAAGCGCGC
GTAGGTGGTTTGTTAAGTTGGATGTGAAAGCCCCG
GGCTCAACCTGGGAACTGCATCCAAAACTGGCAAG
CTAGAGTATGGTAGAGGGTGGTGGAATTTCCTGTG
TAGCGGTGAAATGCGTAGATATAGGAAGGAACACC
AGTGGCGAAGGCGACCACCTGGACTGATACTGACA
CTGAGGTGCGAAAGCGTGGGGAGCAAACAGGATTA GATACCCTGGTAGTCCACGCCGTAAACGATGTCAA
CTAGCCGTTGGGAGCCTTGAGCTCTTAGTGGCGCA
GCTAACGCATTAAGTTGACCGCCTGGGGAGTACGG
CCGCAAGGTTAAAACTCAAATGAATTGACGGGGGC
CCGCACAAGCGGTGGAGCATGTGGTTTAATTCGAA
GCAACGCGAAGAACCTTACCAGGCCTTGACATCCA
ATGAACTTTCTAGAGATAGATTGGTGCCTTCGGGA
ACATTGAGACAGGTGCTGCATGGCTGTCGTCAGCT
CGTGTCGTGAGATGTTGGGTTAAGTCCCGTAACGA
GCGCAACCCTTGTCCTTAGTTACCAGCACGTTATG
GTGGGCACTCTAAGGAGACTGCCGGTGACAAACCG
GAGGAAGGTGGGGATGACGTCAAGTCATCATGGCC
CTTTCGGCCTGGGCTACACACGTGCTACAATGGTC
GGTACAAAGGGTTGCCAAGCCGCGAGGTGGAGCTA
ATCCCATAAAACCGATCGTAGTCCGGATCGCAGTC
TGCAACTCGACTGCGTGAAGTCGGAATCGCTAGTA
ATCGCGAATCAGAATGTCGCGGTGAATACGTTCCC
GGGCCTTGTACACACCGCCCGTCACACCATGGGAG
TGGGTTGCACCAGAAGTAGCTAGTCTAACCTTCGG
GAGGACGGTTACCACGGTGTGATTCATGACTGGGG
GAAGTCGAAC.

Enterobacter sp. nov 638 (MBI-506)
16S sequence:
                                (SEQ ID No. 4)
ATAATGCAAGTCGAGCGAACTGATTAGAAGCTTGC
TTCTATGACGTTAGCGGCGGACGGGTGAGTAACAC
GTGGGCAACCTGCCTGTAAGACTGGGATAACTTCG
GGAAACCGAAGCTAATACCGGATAGGATCTTCTCC
TTCATGGGAGATGATTGAAAGATGGTTTCGGCTAT
CACTTACAGATGGGCCCGCGGTGCATTAGCTAGTT
GGTGAGGTAACGGCTCACCAAGGCAACGATGCATA
GCCGACCTGAGAGGGTGATCGGCCACACTGGGACT
GAGACACGGCCCAGACTCCTACGGGAGGCAGCAGT
AGGGAATCTTCCGCAATGGACGAAAGTCTGACGGA
GCAACGCCGCGTGAGTGATGAAGGCTTTCGGGTCG
TAAAACTCTGTTGTTAGGGAAGAACAAGTACAAGA
GTAACTGCTTGTACCTTGACGGTACCTAACCAGAA
AGCCACGGCTAACTACGTGCCAGCAGCCGCGGTAA
TACGTAGGTGGCAAGCGTTATCCGGAATTATTGGG
CGTAAAGCGCGCGCAGGCGGTTTCTTAAGTCTGAT
GTGAAAGCCCACGGCTCAACCGTGGAGGGTCATTG
GAAACTGGGGAACTTGAGTGCAGAAGAGAAAAGCG -continued
GAATTCCACGTGTAGCGGTGAAATGCGTAGAGATG

TGGAGGAACACCAGTGGCGAAGGCGGCTTTTTGGT

CTGTAACTGACGCTGAGGCGCGAAAGCGTGGGGAG

CAAACAGGATTAGATACCCTGGTAGTCCACGCCGT

AAACGATGAGTGCTAAGTGTTAGAGGGTTTCCGCC

CTTTAGTGCTGCAGCTAACGCATTAAGCACTCCGC

CTGGGGAGTACNGGTCGCAAGACTGAAACTCAAAG

GAATTGACGGGGGCCCGCACAAGCGGTGGAGCATG

TGGTTTAATTCGAAGCAACGCGAAGAACCTTACCA

GGTCTTGACATCCTCTGACAACTCTAGAGATAGAG

CGTTCCCCTTCGGGGACAGAGTGACAGGTGGTGC

ATGGTTGTCGTCAGCTCGTGTCGTGAGATGTTGGG

TTAAGTCCCGCAACGAGCGCAACCCTTGATCTTAG

TTGCCAGCATTCAGTTGGGCACTCTAAGGTGACTG

CCGGTGACAAACCGGAGGAAGGTGGGGATGACGTC

AAATCATCATGCCCCTTATGACCTGGGCTACACAC

GTGCTACAATGGATGGTACAAAGGGCTGCAAGACC

GCGAGGTCAAGCCAATCCCATAAAACCATTCTCAG

TTCGGATTGTAGGCTGCAACTCGCCTACATGAAGC

TGGAATCGCTAGTAATCGCGGATCAGCATGCCGCG

GTGAATACGTTCCCGGGCCTTGTACACACCGCCCG

TCACACCACGAGAGTTTGTAACACCCGAAGTCGGT

GGAGTAACCGTAAGGAGCTAGCCGCCTAAGGTGGG

ACAGATGATTGGGGTG.

*Burkholderia megapolitana* 0437 16S
sequence:
(SEQ ID No. 5)
CTTCCTGCAGTCGAACGGCAGCGCGGGAGCAATCC

TGGCGGCGAGTGGCGAACGGGTGAGTAATACATCG

GAACGTGTCCTGTAGTGGGGGATAGCCCGGCGAAA

GCCGGATTAATACCGCATACGCTCTACGGAGGAAA

GGGGGGGATCTTAGGACCTCTCGCTACAGGGGCGG

CCGATGCGGATTAGCTAGTTGGTGGGGTAAAGGC

CTACCAAGGCGACGATCCGTAGCTGGTCTGAGAGG

ACGACCAGCCACACTGGGACTGAGACACGGCCCAG

ACTCCTACGGGAGGCAGCAGTGGGGAATTTTGGAC

AATGGGGGCAACCCTGATCCAGCAATGCCGCGTGT

GTGAAGAAGGCCTTCGGGTTGTAAAGCACTTTTGT

CCGGAAAGAAATCATCCTGGTTAATACCTGGGGTG

GATGACGGTACCGGAAGAATAAGCACCGGCTAACT

ACGTGCCAGCAGCCGCGGTAATACGTAGGGTGCAA

GCGTTAATCGGAATTACTGGGCGTAAAGCGTGCGC

-continued
AGGCGGTTCGCTAAGACAGATGTGAAATCCCCGGG

CTTAACCTGGGAACTGCATTTGTGACTGGCGGGCT

AGAGTATGGCAGAGGGGGGTAGAATTCCACGTGTA

GCAGTGAAATGCGTAGAGATGTGGAGGAATACCGA

TGGCGAAGGCAGCCCCCTGGGCCAATACTGACGCT

CATGCACGAAAGCGTGGGGAGCAAACAGGATTAGA

TACCCTGGTAGTCCACGCCCTAAACGATGTCAACT

AGTTGTCGGGTCTTCATTGACTTGGTAACGTAGCT

AACGCGTGAAGTTGACCGCCTGGGGAGTACGGTCG

CAAGATTAAAACTCAAAGGAATTGACGGGGACCCG

CACAAGCGGTGGATGATGTGGATTAATTCGATGCA

ACGCGAAAAACCTTACCTACCCTTGACATGTACGG

AATCCTGCTGAGAAGGTGGGAGTGCCCGAAAGGGA

GCCGTAACACAKGTGCTGCATGGGCTGTCGTCAGC

TCGTGTCGTGAGATGTTGGGTTAAGTCCCGCAACG

AGCGCAACCCTTGTCCCTAGTTGCTACGCAAGAGC

ACTCCAGGGAGACTGCCGGTGACAAACCGGAGGAA

GGTGGGGATGACGTCAAGTCCTCATGGCCCTTATG

GGTAGGGCTTCACACGTCATACAATGGTCGGAACA

GAGGGTCGCCAACCCGCAAGGGGGAGCCAATCCCA

GAAAACCGATCGTAGTCCGGATCGCAGTCTGCAAC

TCGACTGCGTGAAGCTGGAATCGCTAGTAATCGCG

GATCAGCATGCCGCGGTGAATACGTTCCCGGGTCT

TGTACACACCGCCCGTCACACCATGGGAGTGGGTT

TTACCAGAAGTGGCTAGTCTAACCGCAAGGAGGAC

GGTCACCACGGTAGGATTCATGACTGGGGGAAGTC

GA.

*Flavobacterium sacchrophilum* R129
16S sequence:
(SEQ ID No. 6)
TATACGATGAAGAGTTTGATCCTGGCTCAGGATGA

ACGCTAGCGGCAGGCTTAACACATGCAAGTCGAGG

GGTATAGTTCTTCGGAACTAGAGACCGGCGCACGG

GTGCGTAACGCGTATGCAATCTACCTTTTACAGAG

GGATAGCCCAGAGAAATTTGGATTAATACCTCATA

GTATTATGAAATGGCATCATTTTATAATTAAAGTC

ACAACGGTAAAAGATGAGCATGCGTCCCATTAGCT

AGTTGGTAAGGTAACGGCTTACCAAGGCTACGATG

GGTAGGGGTCCTGAGAGGGAGATCCCCCACACTGG

TACTGAGACACGGACCAGACTCCTACGGGAGGCAG

CAGTGAGGAATATTGGACAATGGGCGCAAGCCTGA

TCCAGCCATGCCGCGTGCAGGATGACGGTCCTATG

-continued
```
GATTGTAAACTGCTTTTATACGAGAAGAAACACTC
CGACGTGTCGGAGCTTGACGGTATCGTAAGAATAA
GGATCGGCTAACTCCGTGCCAGCAGCCGCGGTAAT
ACGGAGGATCCAAGCGTTATCCGGAATCATTGGGT
TTAAAGGGTCCGTAGGCGGTTTAATAAGTCAGTGG
TGAAAGCCCATCGCTCAACGGTGGAACGGCCATTG
ATACTGTTAAACTTGAATTATTAGGAAGTAACTAG
AATATGTAGTGTAGCGGTGAAATGCTTAGAGATTA
CATGGAATACCAATTGCGAAGGCAGGTTACTACTA
ATGGATTGACGCTGATGGACGAAAGCGTGGGTAGC
GAACAGGATTAGATACCCTGGTAGTCCACGCCGTA
AACGATGGATACTAGCTGTTGGAAGCAATTTCAGT
GGCTAAGCGAAAGTGATAAGTATCCCACCTGGGGA
GTACGTTCGCAAGAATGAAACTCAAAGGAATTGAC
GGGGGCCCGCACAAGCGGTGGAGCATGTGGTTTAA
TTCGATGATACGCGAGGAACCTTACCAAGGCTTAA
ATGTAGTTTGACCGATTTGGAAACAGATCTTTCGC
AAGACAAATTACAAGGTGCTGCATGGTTGTCGTCA
GCTCGTGCCGTGAGGTGTCAGGTTAAGTCCTATAA
CGAGCGCAACCCCTGTTGTTAGTTGCCAGCGAGTC
ATGTCGGGAACTCTAACAAGACTGCCAGTGCAAAC
TGTGAGGAAGGTGGGGATGACGTCAAATCATCACG
GCCCTTACGCCTTGGGCTACACACGTGCTACAATG
GCCGGTACAGAGAGCAGCCACTGGGCGACCAGGAG
CGAATCTATAAAACCGGTCACAGTTCGGATCGGAG
TCTGCAACTCGACTCCGTGAAGCTGGAATCGCTAG
TAATCGGATATCAGCCATGATCCGGTGAATACGTT
CCCGGGCCTTGTACACACCGCCCGTCAAGCCATGG
AAGCTGGGGGTGCCTGAAGTCGGTGACCGCAAGGA
GCTGCCTAGGGTAAAACTGGTAACTAGGGCTAAGT
CGTAACAAGGTAGCCGTACCGGAAGGTGCGGCTGG
AACACCTCCTTTCTA.
```

Ramularia sp. R223 ITS sequence:
(SEQ ID No. 7)
```
CGGAGGGATCATTACTGAGTGAGGGAGCAGTCCCG
ACCTCCAACCCTTTGTGAACGCATCATGTTGCTTT
GGGGGCGACCCTGCCGTCCGCGGCATTCCCCCCGA
AGGTCATCAAAACACTGCATTCTTACGTCGGAGTA
TAAAGTTAATTTAATAAAACTTTCAACAACGGATC
TCTTGGTTCTGGCATCGATGAAGAACGCAGCGAAA
TGCGATAAGTAATGTGAATTGCAGAATTCAGTGAA
TCATCGAATCTTTGAACGCACATTGCGCCCCCTGG
```

-continued
```
TATTCCGGGGGGCATGCCTGTTCGAGCGTCATTTC
ACCACTCAAGCCTCGCTTGGTATTGGGCGTCGCGA
GTCTCTCGCGCGCCTCAAAGTCTCCGGCTGAGCGG
TTCGTCTCCCAGCGTTGTGGCAACTATTTCGCAGT
GGAGTTCGAGTCGTCGCGGCCGTTAAATCTTTCAA
AGGTTGACCTCGGATCAGGTAGGGATACCCGCTGA
ACTTAAGCAT.
```

Streptomyces sp. R518 16S sequence:
(SEQ ID No. 8)
```
CGTGGGCAATCTGCCCTTCACTCTGGGACAAGCCC
TGGAAACGGGGTCTAATACCGGATACCACTACCGC
AGGCATCTGTGGTGGTTGAAAGCTCCGGCGGTGAA
GGATGAGCCCGCGGCCTATCAGCTTGTTGGTGAGG
TAATGGCTCACCAAGGCGACGACGGGTAGCCGGCC
TGAGAGGGCGACCGGCCACACTGGGACTGAGACAC
GGCCCAGACTCCTACGGGAGGCAGCAGTGGGGAAT
ATTGCACAATGGGCGAAAGCCTGATGCAGCGACGC
CGCGTGAGGGATGACGGCCTTCGGGTTGTAAACCT
CTTTCAGCAGGGAAGAAGCGAAAGTGACGGTACCT
GCAGAAGAAGCGCCGGCTAACTACGTGCCAGCAGC
CGCGGTAATACGTAGGGCGCAAGCGTTGTCCGGAA
TTATTGGGCGTAAAGAGCTCGTAGGCGGCTTGTCA
CGTCGGGTGTGAAAGCCCGGGGCTTAACCCCGGGT
CTGCATTCGATACGGGCTAGCTAGAGTGTGGTAGG
GGAGATCGGAATTCCTGGTGTAGCGGTGAAATGCG
CAGATATCAGGAGGAACACCGGTGGCGAAGGCGGA
TCTCTGGGCCATTACTGACGCTGAGGAGCGAAAGC
GTGGGGAGCGAACAGGATTAGATACCCTGGTAGTC
CACGCCGTAAACGGTGGGAACTAGGTGTTGGCGAC
ATTCCACGTCGTCGGTGCCGCAGCTAACGCATTAA
GTTCCCCGCCTGGGGAGTACGGCCGCAAGGCTAAA
ACTCAAAGGAATTGACGGGGGCCCGCACAAGCAGC
GGAGCATGTGGCTTAATTCGACGCAACGCGAAGAA
CCTTACCAAGGCTTGACATACGCCGGAAAGCATCA
GAGATGGTGCCCCCCTTGTGGTCGGTGTACAGGTG
GTGCATGGCTGTCGTCAGCTCGTGTCGTGAGATGT
TGGGTTAAGTCCCGCAACGAGCGCAACCCTTGTCC
TGTGTTGCCAGCATGCCCTTCGGGGTGATGGGGAC
TCACAGGAGACCGCCGGGGTCAACTCGGAGGAAGG
TGGGGACGACGTCAAGTCATCATGCCCCTTATGTC
TTGGGCTGCACACGTGCTACAATGGCAGGTACAAT
```

-continued
GAGCTGCGATACCGTGAGGTGGAGCGAATCTCAAA

AAGCCTGTCTCAGTTCGGATTGGGGTCTGCAACTC

GACCCCATGAAGTCGGAGTTGCTAGTAATCGCAGA

TCAGCATTGCTGCGGTGAATACGTTCCCGGGCCTT

GTACACACCGCCCGTCACGTCACGAAAGTCGGTAA

CACCCGAAGCCGGTGGCCCAACCCCTTGTGGGAGG

GAGCTGTCGAAGGTGGGACTGGCGA.

Streptomyces laurentii R914
16S sequence:
(SEQ ID No. 9)
TGCAGTCGAACGATGAAGCCCTTCGGGGTGGATTA

GTGGCGAACGGGTGAGTAACACGTGGGCAATCTGC

CCTTCACTCTGGGACAAGCCCTGGAAACGGGGTCT

AATACCGGATACGACCTGGGAAGGCATCTTCTCGG

GTGGAAAGCTCCGGCGGTGAAGGATGAGCCCGCGG

CCTATCAGCTTGTTGGTGAGGTAACGGCTCACCAA

GGCGACGACGGGTAGCCGGCCTGAGAGGGCGACCG

GCCACACTGGGACTGAGACACGGCCCAGACTCCTA

CGGGAGGCAGCAGTGGGGAATATTGCACAATGGGC

GAAAGCCTGATGCAGCGACGCCGCGTGAGGGATGA

CGGCCTTCGGGTTGTAAACCTCTTTCAGCAGGGAA

GAAGCGAAAGTGACGGTACCTGCAGAAGAAGCGCC

GGCTAACTACGTGCCAGCAGCCGCGGTAATACGTA

GGGCGCAAGCGTTGTCCGGAATTATTGGGCGTAAA

GAGCTCGTAGGCGGCTTGTCACGTCGGGTGTGAAA

GCCCGGGGCTTAACCCCGGGTCTGCATCCGATACG

GGCAGGCTAGAGTGTGGTAGGGGAGATCGGAATTC

CTGGTGTAGCGGTGAAATGCGCAGATATCAGGAGG

AACACCGGTGGCGAAGGCGGATCTCTGGGCCATTA

CTGACGCTGAGGAGCGAAAGCGTGGGGAGCGAACA

GGATTAGATACCCTGGTAGTCCACGCCGTAAACGT

TGGGAACTAGGTGTTGGCGACATTCCACGTTGTCG

GTGCCGCAGCTAACGCATTAAGTTCCCCGCCTGGG

GAGTACGGCCGCAAGGCTAAAACTCAAAGGAATTG

ACGGGGCCCGCACAAGCAGCGGAGCATGTGGCTT

AATTCGACGCAACGCGAAGAACCTTACCAAGGCTT

GACATATACCGGAAACATCCAGAGATGGGTGCCCC

CTTGTGGTCGGTATACAGGTGGTGCATGGCTGTCG

TCAGCTCGTGTCGTGAGATGTTGGGTTAAGTCCCG

CAACGAGCGCAACCCTTGTCCTGTGTTGCCAGCAT

GCCCTTCGGGGTGATGGGACTCACAGGAGACCGC

CGGGGTCAACTCGGAGGAAGGTGGGGACGACGTCA

-continued
AGTCATCATGCCCCTTATGTCTTGGGCTGCACACG

TGCTACAATGGCCGGTACAAAGAGCTGCGATGCCG

TGAGGCGGAGCGAATCTCAAAAAGCCGGTCTCAGT

TCGGATTGGGGTCTGCAACTCGACCCCATGAAGTC

GGAGTTGCTAGTAATCGCAGATCAGCATTGCTGCG

GTGAATACGTTCCCGGGCCTTGTACACACCGCCCG

TCACGTCACGAAAGTCGGTAACACCCGAAGCCGGT

GGCCCAACCCCTTGTGGGAGGGAGCTGTCGAAGGT

GGGACTGGCGAT.

Bacillus safensis R950 16S sequence:
(SEQ ID No. 10)
GTCGAGCGGACAGAAGGGAGCTTGCTCCCGGATGT

TAGCGGCGGACGGGTGAGTAACACGTGGGTAACCT

GCCTGTAAGACTGGGATAACTCCGGGAAACCGGAG

CTAATACCGGATAGTTCCTTGAACCGCATGGTTCA

AGGATGAAAGACGGTTTCGGCTGTCACTTACAGAT

GGACCCGCGGCGCATTAGCTAGTTGGTGGGGTAAT

GGCTCACCAAGGCGACGATGCGTAGCCGACCTGAG

AGGGTGATCGGCCACACTGGGACTGAGACACGGCC

CAGACTCCTACGGGAGGCAGCAGTAGGGAATCTTC

CGCAATGGACGAAAGTCTGACGGAGCAACGCCGCG

TGAGTGATGAAGGTTTTCGGATCGTAAAGCTCTGT

TGTTAGGGAAGAACAAGTGCGAGAGTAACTGCTCG

CACCTTGACGGTACCTAACCAGAAAGCCACGGCTA

ACTACGTGCCAGCAGCCGCGGTAATACGTAGGTGG

CAAGCGTTGTCCGGAATTATTGGGCGTAAAGGGCT

CGCAGGCGGTTTCTTAAGTCTGATGTGAAAGCCCC

CGGCTCAACCGGGAGGGTCATTGGAAACTGGGAA

ACTTGAGTGCAGAAGAGGAGAGTGGAATTCCACGT

GTAGCGGTGAAATGCGTAGAGATGTGGAGGAACAC

CAGTGGCGAAGGCGACTCTCTGGTCTGTAACTGAC

GCTGAGGAGCGAAAGCGTGGGGAGCGAACAGGATT

AGATACCCTGGTAGTCCACGCCGTAAACGATGAGT

GCTAAGTGTTAGGGGGTTTCCGCCCCTTAGTGCTG

CAGCTAACGCATTAAGCACTCCGCCTGGGGAGTAC

GGTCGCAAGACTGAAACTCAAAGGAATTGACGGGG

GCCCGCACAAGCGGTGGAGCATGTGGTTTAATTCG

AAGCAACGCGAAGAACCTTACCAGGTCTTGACATC

CTCTGACAACCCTAGAGATAGGGCTTTCCCTTCGG

GGACAGAGTGACAGGTGGTGCATGGTTGTCGTCAG

CTCGTGTCGTGAGATGTTGGGTTAAGTCCCGCAAC

GAGCGCAACCCTTGATCTTAGTTGCCAGCATTCAG

-continued

```
TTGGGCACTCTAAGGTGACTGCCGGTGACAAACCG

GAGGAAGGTGGGGATGACGTCAAATCATCATGCCC

CTTATGACCTGGGCTACACACGTGCTACAATGGAC

AGAACAAAGGGCTGCAAGACCGCAAGGTTTAGCCA

ATCCCATAAATCTGTTCTCAGTTCGGATCGCAGTC

TGCAACTCGACTGCGTGAAGCTGGAATCGCTAGTA

ATCGCGGATCAGCATGCCGCGGTGAATACGTTCCC

GGGCCTTGTACACACCGCCCGTCACACCACGAGAG

TTTGCAACACCCGAAGTCGGTGAGGTAACCTTTAT

GGAGCCAGCCGCCGAAGGTGGGGCAGATGA.
```

Trichoderma sp. S089 ITS sequence:
(SEQ ID No. 11)
```
GAGGGATCATTACCGAGTTTACAACTCCCAAACCC

AATGTGAACGTTACCAAACTGTTGCCTCGGCGGA

TCTCTGCCCCGGGTGCGTCGCAGCCCCGGACCAAG

GCGCCCGCCGGAGGACCAACCAAAACTCTTTTTGT

ATACCCCCTCGCGGGTTTTTTATAATCTGAGCCTT

CTCGGCGCCTCTCGTAGGCGTTTCGAAAATGAATC

AAAACTTTCAACAACGGATCTCTTGGTTCTGGCAT

CGATGAAGAACGCAGCGAAATGCGATAAGTAATGT

GAATTGCAGAATTCAGTGAATCATCGAATCTTTGA

ACGCACATTGCGCCCGCCAGTATTCTGGCGGGCAT

GCCTGTCCGAGCGTCATTTCAACCCTCGAACCCCT

CCGGGGGGTCGGCGTTGGGGATCGGCCCTGCCTCT

TGGCGGTGGCCGTCTCCGAAATACAGTGGCGGTCT

CGCCGCAGCCTCTCCTGCGCAGTAGTTTGCACACT

CGCATCGGGAGCGCGGCGCGTCCACAGCCGTTAAA

CACCCAACTTCTGAAATGTTGACCTCGGATCAGGT

AGGAATACCCGCTGAACTTAAGC.
```

Example 2. Microbe Characteristics

| Microbe | Phosphate Solubilization | ACC Deaminase | IAA Production | CAS | AMS |
|---|---|---|---|---|---|
| H492 | − | − | − | − | − |
| H491 | +++ | +++ | + | − | ++ |
| MBI-401 | +++ | | +++ | +++ | |
| MBI-506 | + | − | + | − | − |
| O437 | Possible | | | | |

Example 3. Yield and Drought Improvements on Corn

Field trials were conducted in CA, USA during growing season. Sweet corn was planted in the field. Four replicates of seven to nine plants per treatment were used in a randomized design. Two treatments were conducted with 25 ml per plant applied for each treatment. Plants were either provided grower-standard water volumes or 50% of the standard water rate. Corn was harvested at an appropriate time for the crop and total weight per plot, weight per ear and number of marketable ears were assessed. Details are shown in FIGS. 1-6.

For MBI-508, field trials were conducted in CA, USA during growing season. Sweet corn was planted in the field. Four replicates of seven plants per treatment were used in a randomized design. Two treatments were conducted with 25 ml of MBI-507 at 30 g/L per plant applied for each treatment. Plants were either provided grower-standard water volumes or 50% of the standard water rate. Corn was harvested at an appropriate time for the crop and total weight per plot, weight per ear and number of marketable ears were assessed.

Example 4. Drought Tolerance

Figure 7:
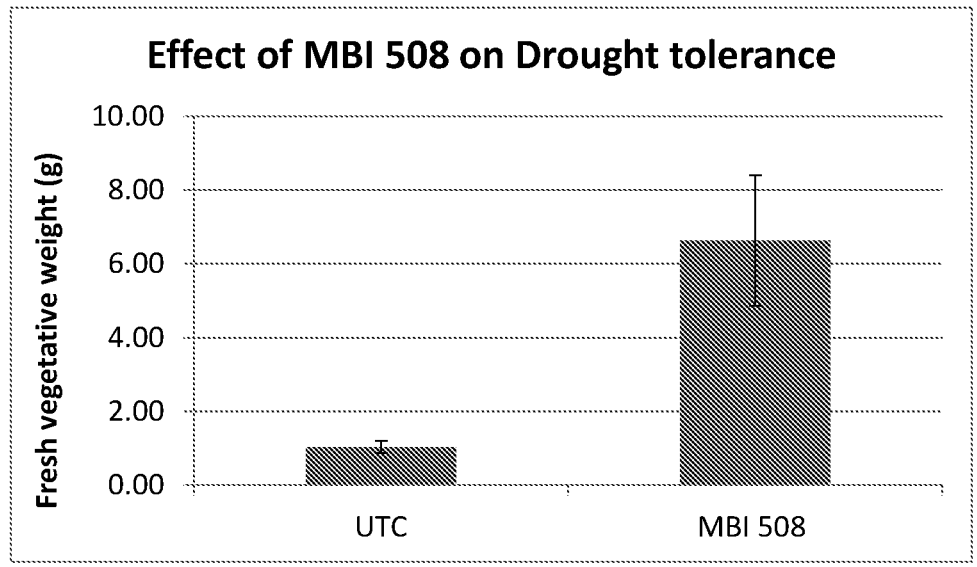
FIG. 7 denotes effect of MBI 508 on drought tolerance. Y-Axis is fresh vegetative weight. UTC stands for untreated control.

FIG. 7 denotes effect of MBI 508 on drought tolerance.

Example 5. Yield and Drought Improvements on Tomatoes

Figure 8:
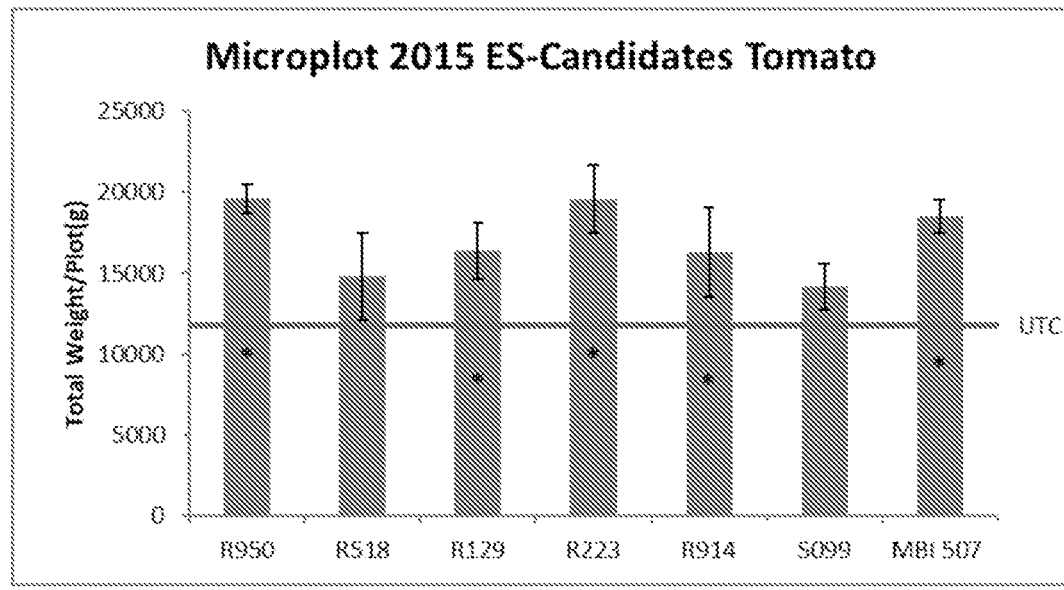
FIG. 8 denotes total weight/plot (g) of carious strains on tomato. Evaluation treatment p-value<0.220 and Rsq=0.5830. Error bars represent standard error. UTC stands for untreated control.
Figure 9:
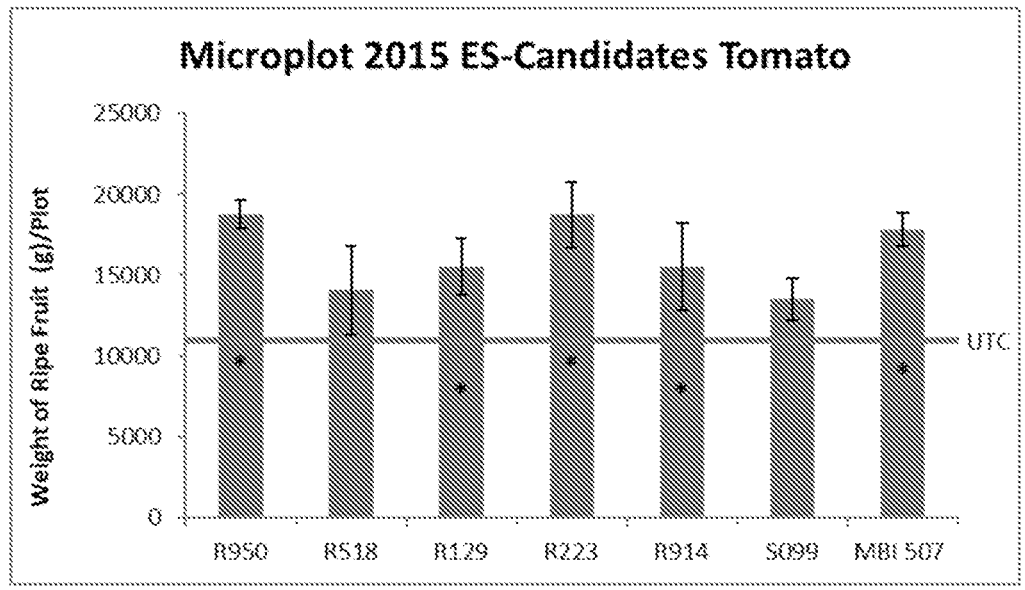
FIG. 9 denotes weight of ripe fruit (g)/plot of various strains on tomato. UTC stands for untreated control.
Figure 10:
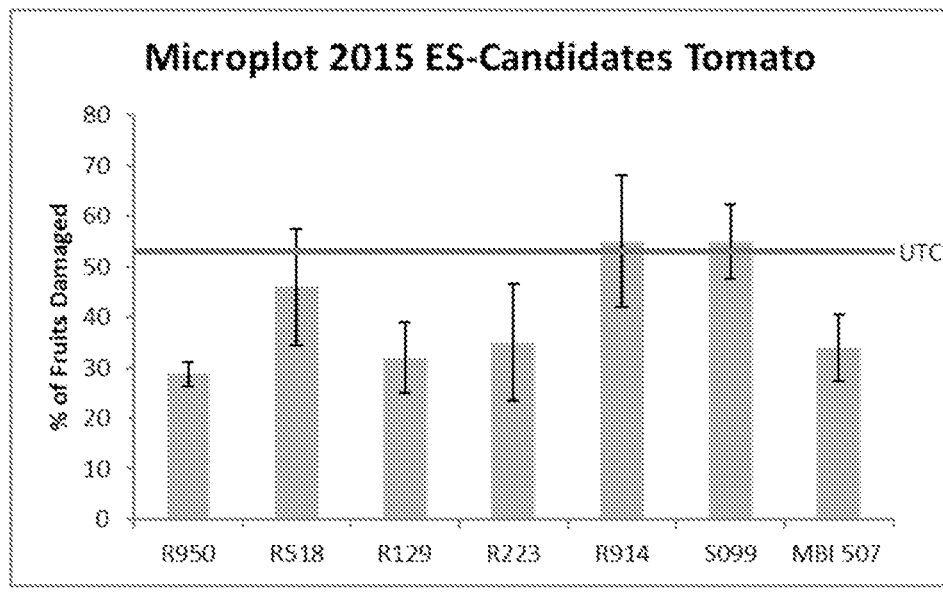
FIG. 10 denotes % of fruits damage of various strains on tomato. UTC stands for untreated control.

Field trials were conducted in CA, USA during growing season. Roma tomato seedlings were transplanted in to the field. Five replicates of six plants per treatment were used in a randomized design. Two treatments were conducted with 10 ml per plant applied and 40 ml per plant applied 7 days later. Fruit was harvested at an appropriate time for the crop and total weight per plot, weight of ripe fruit per plot and quantity of damaged fruits were assessed. Details are shown in FIGS. 8-10.

Example 6. Additional Tests

Figure 11:
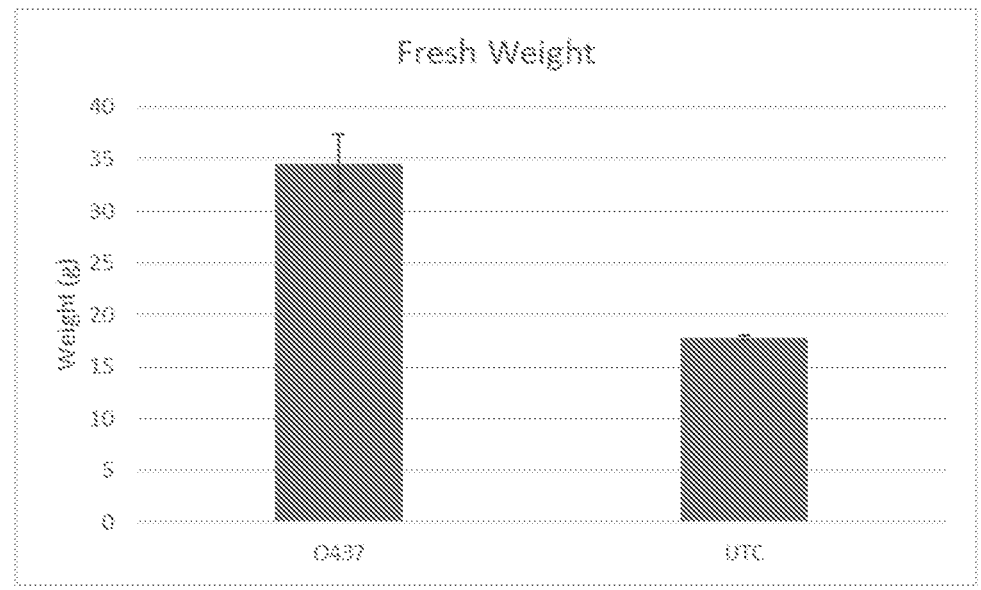
FIG. 11 denotes microbe *Burkholderia megapolitana* O437 evaluated for plant health effects on corn plants. UTC stands for untreated control.
Figure 12:
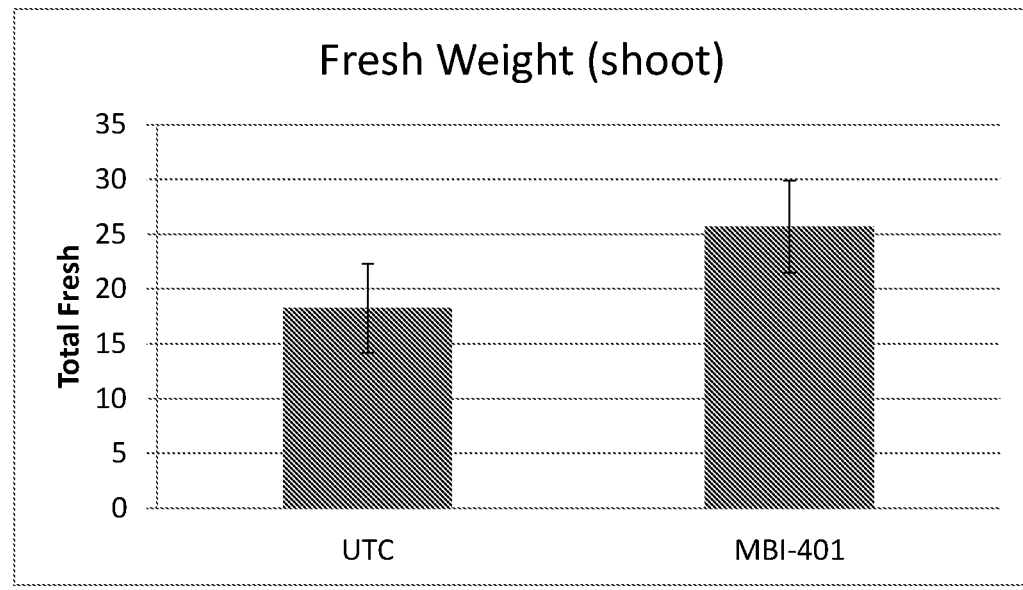
FIG. 12 denotes microbe *Pseudomonas protegens* CL45A evaluated for plant health effects on plants. UTC stands for untreated control.
Figure 13:
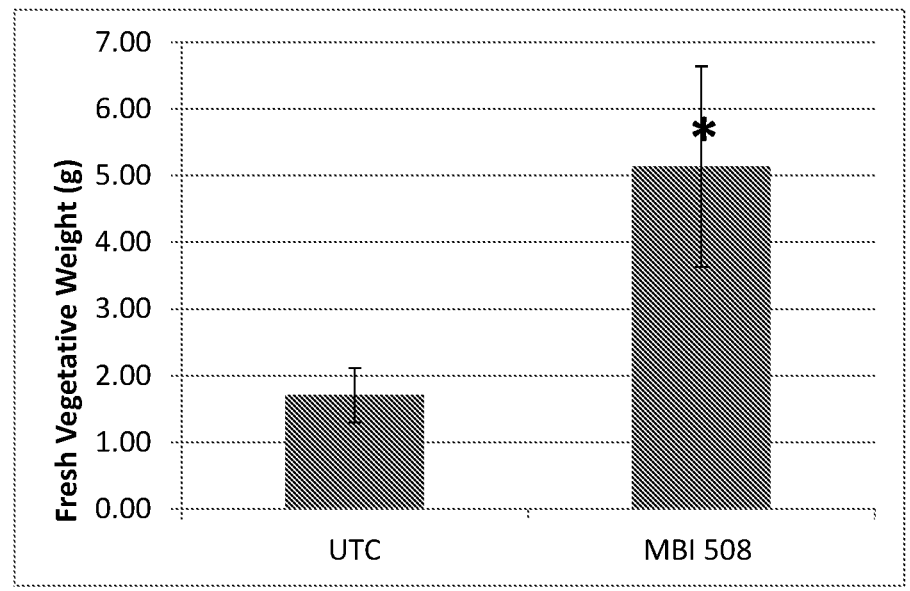
FIG. 13 denotes effect of MBI 508 on Salinity tolerance. UTC stands for untreated control.
Figure 14:
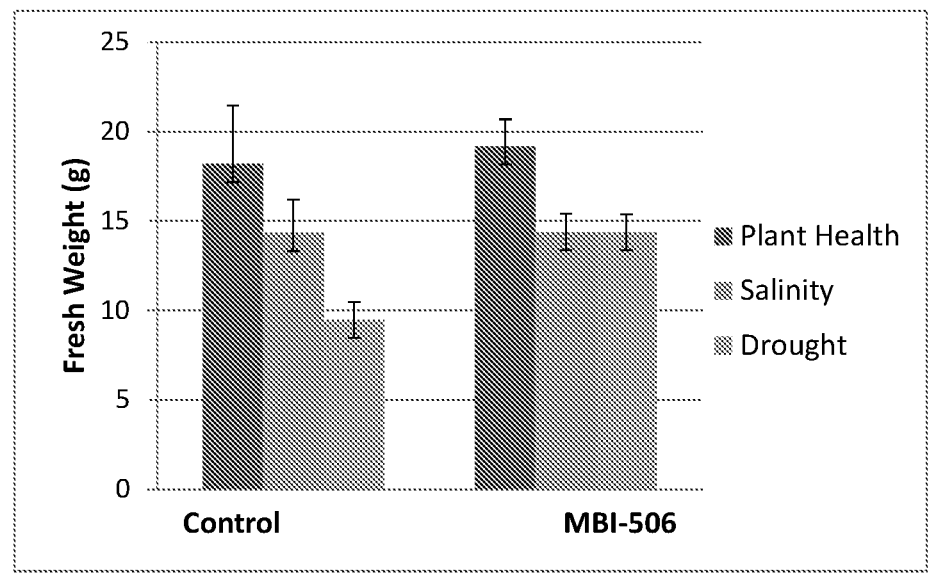
FIG. 14 denotes stress reduction of MBI 506. UTC stands for untreated control.
Figure 15:
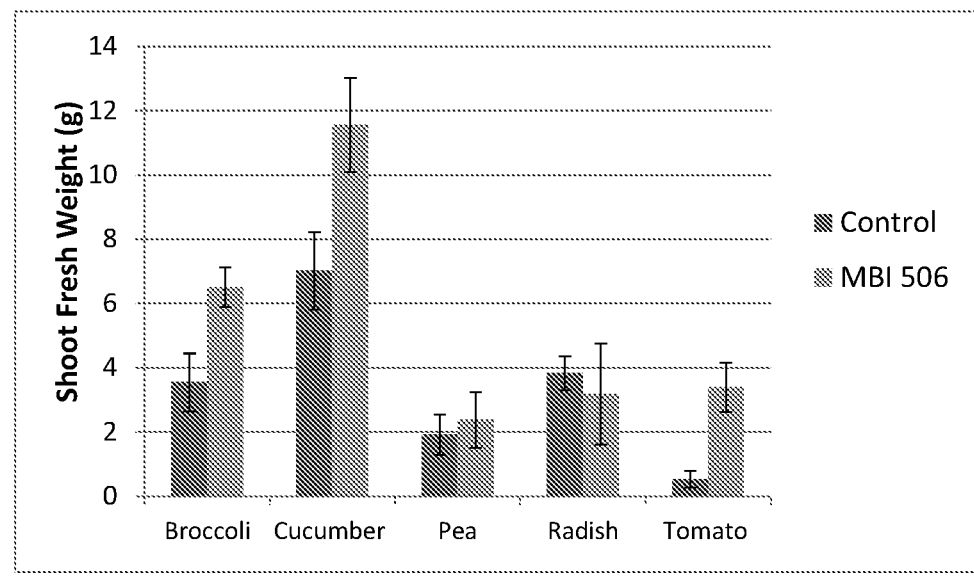
FIG. 15 denotes plant health effects of MBI 506 on various plants. UTC stands for untreated control.
Figure 16:
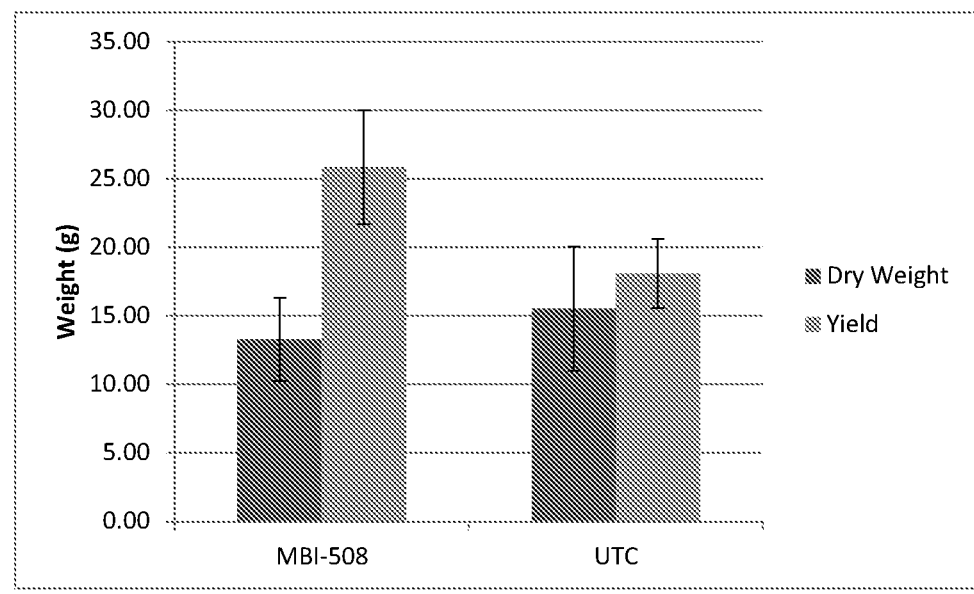
FIG. 16 denotes fresh weight effects on MBI 506 in radish. UTC stands for untreated control.

Candidate microbe *Burkholderia megapolitana* O437 was evaluated for plant health effects on corn plants. Three replicates of per treatment were conducted with each replicate consisting of three plants per pot. Drench application was performed one week after planting and 30 ml was drenched per pot. Total fresh weight was collected. The results are shown in FIG. 11.

Additional microbes were tested under various stress tolerance and improve yield conditions as denoted in FIGS. 12-16.

Microorganism deposits Strains *Flavobacterium hawaineses* nov sp. H492 (NRRL B-50584), *Bacillus megaterium* H491 (NRRL B-50769), *Pseudomonas protegens* (previously fluorescens) CL45A (ATCC 55799), and *Enterobacter* sp. nov 638 (PTA-11727) are bacteria and were already deposited by one ordinary skilled in the art.

Purified cultures of the microbial (bacteria or fungi) strains identified herein as *Trichoderma* sp. S089, *Bacillus safensis* R950; *Streptomyces* sp. R518; *Burkholderia megapolitana* O437; *Flavobacterium sacchrophilum* R129; *Ramularia* sp. R223; and *Streptomyces laurentii* R914 were deposited under the terms of the Budapest Treaty on 31 May 2019 with the Agricultural Research Culture Collection (NRRL), 1815 N. University Street, Peoria, Ill. 61604 USA, and given the following number:

| Microbe | Deposit | Date |
|---|---|---|
| Trichoderma sp. S089 | 67808 | 31 May 2019 |
| Bacillus safensis R950 | B-67775 | 31 May 2019 |

| Microbe | Deposit | Date |
| --- | --- | --- |
| *Streptomyces* sp. R518 | B-67773 | 31 May 2019 |
| *Burkholderia* megapolitana O437 | B-67776 | 31 May 2019 |
| *Flavobacterium* sacchrophilum R129 | B-67772 | 31 May 2019 |
| *Ramularia* sp. R223 | 67807 | 31 May 2019 |
| *Streptomyces laurentii* R914 | B-67774 | 31 May 2019 |

As such, all of the microbial strains have been deposited under conditions that ensure that access to the cultures will be available during the pendency of this patent application to one determined by the Commissioner of Patents and Trademarks to be entitled thereto under 37 C.F.R. § 1.14 and 35 U.S.C. § 122. The deposits represent substantially pure cultures of the deposited strains. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A method to improve yield and/or drought tolerance of a plant or seed of corn, spinach, or tomatoes, comprising:
applying an effective amount of a composition to the plant or seed to improve yield and/or drought tolerance of the plant or seed as compared to a control plant or seed, the composition comprising:

a microorganism whole cell broth collected from fermentation of *Bacillus safensis* R950 and including *Bacillus safensis* R950; and a carrier, diluent, or adjuvant.

2. The method of claim 1, wherein the composition is applied as a foliar treatment.

3. The method of claim 1, wherein the composition is applied to a growth medium for the plant or seed as a drip, spray, irrigation or soil drench.

4. The method of the claim 1, wherein applying the effective amount of the composition to the plant or seed thereof causes one or more of the following: increased yield, increased biomass, increased grain weight per plot or per plant, improved nutritional content, greater resistance to lodging, increased root length, increased drought stress tolerance, increased harvest index, increased fresh ear weight, increased ear length, increased ear diameter, increased ear weight, increased seed number, increased seed weight, and/or increased bushels per acre.

5. A method to improve yield and/or drought tolerance of a plant or seed of corn, spinach, or tomatoes, comprising the step of: applying an effective amount of a composition comprising *Bacillus safensis* R950 to the plant or seed, to improve yield and/or drought tolerance as compared to a control plant and/or seed.

6. The method of claim 5, wherein the composition is applied as a foliar treatment.

7. The method of claim 5, wherein the composition is applied to a growth medium for the plant or seed as a drip, spray, irrigation or soil drench.

8. The method of the claim 5, wherein applying the effective amount of the composition to the plant or seed causes one or more of the following: increased yield, increased biomass, increased grain weight per plot or per plant, improved nutritional content, greater resistance to lodging, increased root length, increased drought stress tolerance, increased harvest index, increased fresh ear weight, increased ear length, increased ear diameter, increased ear weight, increased seed number, increased seed weight, and/or increased bushels per acre.

9. The method of claim 5, wherein the *Bacillus safensis* R950 comprises *Bacillus safensis* R950 deposited under accession number NRRL-B-67775.

10. The method of claim 1, wherein the composition further comprises a pesticidal agent.

11. The method of claim 10, wherein the pesticidal agent is one or more of a fungicide, herbicide, insecticide, miticide, acaricide, nematicide, or gastropodicide.

12. The method of claim 10, wherein the pesticidal agent is selected from the group consisting of ipconozole, metalaxyl, azoxystrobin, prothioconazole, fluoxastrobin, clothianidin, *Bacillus firmus, Penicillium bilaiae, Trichoderma virens*, and *Bacillus amyloliquefaciens*.

13. The method of claim 1, further comprising a plant nutrient or fertilizer.

14. The method of claim 1, wherein the composition is formulated as a solid, liquid or gel.

15. The method of claim 1, wherein the composition is formulated as a powder, lyophilisate, pellet or granules.

16. The method of claim 1, wherein the composition is formulated as an emulsion, colloid, suspension or solution.

17. The method of claim 1, wherein the microorganism whole cell broth has a concentration of from $1\times10^1$ to $1\times10^{15}$ colony forming units of *Bacillus safensis* R950 per milliliter of the whole cell broth.

* * * * *